(12) United States Patent
Hirano et al.

(10) Patent No.: US 8,829,045 B2
(45) Date of Patent: Sep. 9, 2014

(54) AGROCHEMICAL COMPOSITION FOR PEST CONTROL AND PEST CONTROL METHOD

(75) Inventors: Kohji Hirano, Kusatsu (JP); Kouichi Yamaguchi, Chiyoda-ku (JP); Makiko Ohasa, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 285 days.

(21) Appl. No.: 13/258,469

(22) PCT Filed: Mar. 26, 2010

(86) PCT No.: PCT/JP2010/055314
§ 371 (c)(1),
(2), (4) Date: Sep. 22, 2011

(87) PCT Pub. No.: WO2010/113775
PCT Pub. Date: Oct. 7, 2010

(65) Prior Publication Data
US 2012/0016022 A1    Jan. 19, 2012

(30) Foreign Application Priority Data
Mar. 31, 2009 (JP) ................................. 2009-084618

(51) Int. Cl.
*A01N 55/04* (2006.01)
*A01N 37/02* (2006.01)

(52) U.S. Cl.
CPC ....................................... *A01N 55/04* (2013.01)
USPC ........................................... 514/493; 514/552

(58) Field of Classification Search
CPC .............................. A01N 37/02; A01N 55/04
USPC ................................................. 514/493, 552
See application file for complete search history.

(56) References Cited

U.S. PATENT DOCUMENTS

| 3,657,451 A | 4/1972 | Horne, Jr. |
| 6,458,745 B1 | 10/2002 | Runge et al. |
| 2001/0034368 A1 | 10/2001 | Arimoto et al. |

FOREIGN PATENT DOCUMENTS

| CN | 101156591 A | | 4/2008 |
| EP | 0 057 035 A2 | | 8/1982 |
| JP | 54 6609 | | 1/1979 |
| JP | 10067602 | * | 3/1998 |
| JP | 10 251104 | | 9/1998 |
| JP | 2001 501959 | | 2/2001 |
| JP | 3738430 B2 | | 1/2006 |

OTHER PUBLICATIONS

Ahn et al. (J. Econ. Entomol., vol. 86, No. 5, pp. 1334-1338, 1993).*
DOSE ["The Dictionary of Substances and their Effects." (Cambridge, UK, The Royal Scoiety of Chemistry, Thomas Graham House, 1999), pp. 272-274].*
EPA (Retrieved on Feb. 19, 2013 from the Internet: <URL: http://www.epa.gov/oppsrrd1/REDs/factsheets/0245fact.pdf, first published in Sep. 1994).*
Extended European Search Report issued Jun. 29, 2012 in European Patent Application No. 10758547.3.
International Search Report Issued Apr. 27, 2010 in PCT/JP10/055314 Filed Mar. 26, 2010.

* cited by examiner

*Primary Examiner* — Kevin E Weddington
(74) *Attorney, Agent, or Firm* — Oblon, Spivak, McClelland, Maier & Neustadt, L.L.P.

(57) ABSTRACT

An agrochemical composition comprising a propylene glycol fatty acid monoester and fenbutatin oxide in a proportion of 1:150 to 150:1 in terms of a mass ratio (propylene glycol fatty acid monoester:fenbutatin oxide) shows an excellent control effect on pests, hyposensitive mites having reduced sensitivity to chemicals, eggs of mites, and pests other than mites in all stages of growth, even when the composition is applied in a small amount. A pest control method comprising applying the propylene glycol fatty acid monoester and fenbutatin oxide in a proportion of 1:150 to 150:1 in terms of a mass ratio (propylene glycol fatty acid monoester:fenbutatin oxide) to pests or a habitat of the pests also shows an excellent control effect.

14 Claims, No Drawings

AGROCHEMICAL COMPOSITION FOR PEST CONTROL AND PEST CONTROL METHOD

TECHNICAL FIELD

The present invention relates to an agrochemical composition for pest control and a pest control method.

BACKGROUND ART

Chemicals have heretofore been used for controlling pests such as mites, and various compositions have been proposed as chemicals for such pest control chemicals (see, for example, Patent Literature 1 to Patent Literature 3).

Patent Literature 1 discloses a mite control composition comprising a propylene glycol fatty acid monoester and a nonionic surfactant, Patent Literature 2 discloses a mite control composition comprising fenbutatin oxide and a carrier and/or a surfactant, and Patent Literature 3 discloses a composition for controlling pests such as, for example, mites and aphids, which comprises an agricultural chemical component such as, for example, a propylene glycol fatty acid monoester or fenbutatin oxide.

However, the already existing mite control compositions involves a problem that a sufficient control effect necessary for practical use may not be achieved according to application conditions in some cases because of causing such evil that since the mites among pests are easy to bring drug-resistant mindividuals into existence, sufficient control cannot be made, or desired control cannot be made within a certain period of time due to existence of mites having reduced sensitivity to chemicals.

In addition, the mite control compositions are required to ensure the safety of, for example, fishes, shellfishes and domestic animals from the compositions or to reduce the amount of the compositions used, i.e., achieve a high control effect with a small application amount, in addition to the control action on the mites that are an object of control.

CITATION LIST

Patent Literature

Patent Literature 1: Japanese Patent No. 3738430
Patent Literature 2: U.S. Pat. No. 3,657,451
Patent Literature 3: Japanese Patent Application Laid-Open No. 2007-246495

SUMMARY OF INVENTION

Technical Problem

The present invention has been found as a result that researches are repeated on compositions for controlling pests such as mites and has as its object the provision of an agrochemical composition for pest control, by which an excellent control effect is achieved on pests, hyposensitive mites having reduced sensitivity to chemicals and eggs of the mites, and other pests of all stages of growth than the mites even when the composition is applied in a small amount, and a pest control method.

Solution to Problem

An agrochemical composition for pest control according to the present invention comprises a propylene glycol fatty acid monoester and fenbutatin oxide.

In the agrochemical composition for pest control according to the present invention, a mass ratio of the propylene glycol fatty acid monoester to fenbutatin oxide may be generally 1:150 to 150:1, preferably 1:100 to 100:1 though it may not be indiscriminately defined from differences in meteorological conditions, preparation forms, application seasons, application places, kinds and occurrence situations of pests, etc.

A pest control method according to the present invention comprises applying a propylene glycol fatty acid monoester and fenbutatin oxide to pests or a habitat of the pests.

In the pest control method according to the present invention, a mass ratio of the propylene glycol fatty acid monoester to fenbutatin oxide may be generally 1:150 to 150:1, preferably 1:100 to 100:1 though it may not be indiscriminately defined from differences in meteorological conditions, preparation forms, application seasons, application places, kinds and occurrence situations of pests, etc.

In the pest control method according to the present invention, an object of application as the habitat of the pests may be preferably a plant. invention, an object of control may be preferably agricultural pests, particularly preferably at least one agricultural pests selected from the group consisting of mites, aphids, whiteflies and thrips. Among these pests, mites may be preferred, and phytophagous mites may be particularly preferred.

The pest control method according to the present invention may be particularly effective in the case where the object of control is hyposensitive mites having reduced sensitivity to chemicals or eggs of the mites.

In the pest control method according to the present invention, the object of control may be whiteflies, trips or aphids.

Advantageous Effects Of Invention

The agrochemical composition for pest control according to the present invention comprises a selective combination of a propylene glycol fatty acid monoester and fenbutatin oxide as an essential active ingredient, so that a synergistic effect by the two compounds making up this essential active ingredient is produced to develop an excellent pest control action. As a result, a high control effect is achieved even when the composition is applied in a small amount. In addition, high activity is achieved against mites having low sensitivity to a miticide composed of the already existing mite control composition, and markedly excellent ovicidal activity is achieved against eggs of the mites.

Accordingly, according to the agrochemical composition for pest control of the present invention, an excellent control effect is achieved even on hyposensitive mites having reduced sensitivity to chemicals even when the composition is applied in a small amount, and an excellent ovicidal effect is also achieved even on eggs of the mites.

According to the pest control method of the present invention, a propylene glycol fatty acid monoester and fenbutatin oxide are selectively combined for use as chemicals for controlling pests, so that a synergistic effect by these two compounds is produced to develop an excellent pest control action, whereby pests that are an object of control can be efficiently controlled. Although the single use of the propylene glycol fatty acidmonoester or fenbutatin oxide is difficult to control eggs of mites, a markedly excellent ovicidal effect is achieved by selectively combining these compounds for use.

DESCRIPTION OF EMBODIMENTS

The present invention will hereinafter be described in detail.

<Agrochemical Composition for Pest Control>

The agrochemical composition for pest control according to the present invention contains a propylene glycol fatty acid monoester and fenbutatin oxide in synergistically effective amounts as essential active ingredients.

This agrochemical composition for pest control according to the present invention is applied to pests as an object of control. The pests as the object of control may be those of all stages of growth. Specifically, the composition can control pest pupae, pest larvae, pest eggs and mite nymphs, to say nothing of adult pests.

The synergistically effective amounts of the propylene glycol fatty acid monoester and fenbutatin oxide that are essential active ingredients in the agrochemical composition for pest control according to the present invention are indicated by a mass ratio between them. The mass ratio (the propylene glycol fatty acid monoester:fenbutatin oxide) is generally 1:150 to 150:1, preferably 1:100 to 100:1, more preferably 1:50 to 50:1, particularly preferably 1:10 to 10:1 though it may vary according to meteorological conditions, preparation forms, application seasons, application places, kinds and occurrence situations of pests, etc. and thus may not be indiscriminately defined.

The mass ratio of the propylene glycol fatty acid monoester to fenbutatin oxide falls within the above range, whereby the composition comes to develop an excellent pest control action based on the synergistic effect by these two compounds.

Examples of the propylene glycol fatty acid monoester making up the agrochemical composition for pest control according to the present invention include propylene glycol monolaurate, propylene glycol monopalmitate and propylene glycol monooleate.

These compounds may be used either singly or in any combination thereof.

Fenbutatin oxide making up the agrochemical composition for pest control according to the present invention is a compound described on pages 403-404 of "The Pesticide Manual" (Thirteenth Edition; BRITISH CROP PROTECTION COUNCIL).

The agrochemical composition for pest control according to the present invention may contain adjuvants together with the essential active ingredients.

As the adjuvants, may be used general-purpose adjuvants, and examples thereof include carriers, emulsifiers, suspension agents, dispersants, spreading agents, penetrating agents, wetting agents, thickeners, antifoaming agents, stabilizers and antifreezing agents.

Among these, the carriers may be preferably used.

As the carrier, may be used any of a solid carrier and a liquid carrier.

Examples of the solid carrier include vegetable flours (powders) such as starch, active carbon, soybean flour, wheat flour and wood flour; animal powders such as fish meal and milk powder; mineral powders such as talc, kaolin, bentonite, calcium carbonate, zeolite, mirabilite, white carbon, clay and alumina; sulfur powder; and anhydrous sodium sulfate.

On the other hand, examples of the liquid carrier include water; alcohols such as methyl alcohol and ethylene glycol; ketones such as acetone, methyl ethyl ketone and N-methyl-2-pyrrolidone; ethers such as dioxane and tetrahydrofuran; aliphatic hydrocarbons such as kerosine and kerosene; aromatic hydrocarbons such as xylene, trimethylbenzene, tetramethylbenzene, cyclohexane and solvent naphtha; halogenated hydrocarbons such as chloroform and chlorobenzene; amides such as dimethylformamide; esters such as ethyl acetate and glycerol esters of fatty acids; nitriles such as acetonitrile; sulfur-containing compounds such as dimethyl sulfoxide; and vegetable oils such as soybean oil and corn oil.

When the adjuvants are contained together with the essential active ingredients in the agrochemical composition for pest control according to the present invention, the total content of the essential active ingredients, i.e., the total content of the propylene glycol fatty acid monoester and fenbutatin oxide is generally 0.001 to 99 parts by mass and the content of the adjuvants is generally 1 to 99.999 parts by mass though they may vary according to meteorological conditions, preparation forms, application seasons, application places, kinds and occurrence situations of pests, etc. and thus may not be indiscriminately defined. The content of the essential active ingredients and the content of the adjuvants are preferably 0.01 to 95 parts by mass and 5 to 99.99 parts by mass, respectively. The content of the essential active ingredients and the content of the adjuvants are more preferably 0.01 to 90 parts by mass and 10 to 99.99 parts by mass, respectively.

The agrochemical composition for pest control according to the present invention may also contain agricultural chemicals such as, for example, insecticides, fungicides, miticides, nematicides, soil-pesticides, antiviral agents, attractants, herbicides and plant growth regulators as optional active ingredients in addition to the essential active ingredients.

The optional active ingredients are contained, whereby there is a possibility that such a far excellent effect that the pest control effect is more reinforced may be achieved.

Examples of compounds making up active ingredients of the insecticides, miticides, nematicides and soil-pesticides include organic phosphate compounds such as profenofos, dichlorvos, fenamiphos, fenitrothion, EPN, diazinon, chlorpyrifos, chlorpyrifos-methyl, acephate, prothiofos, fosthiazate, cadusafos, dislufoton, isoxathion, isofenphos, ethion, etrimfos, quinalphos, dimethylvinphos, dimethoate, sulprofos, thiometon, vamidothion, pyraclofos, pyridaphenthion, pirimiphos-methyl, propaphos, phosalone, formothion, malathion, tetrachlrovinphos, chlorfenvinphos, cyanophos, trichlorfon, methidathion, phenthoate, ESP, azinphos-methyl, fenthion, heptenophos, methoxychlor, paration, phosphocarb, demeton-5-methyl, monocrotophos, methamidophos, imicyafos, parathion-methyl, terbufos, phosphamidon, phosmet, phorate;

carbamate compounds such as carbaryl, propoxur, aldicarb, carbofuran, thiodicarb, methomyl, oxamyl, ethiofenacarb, pirimicarb, fenobucarb, carbosulfan, benfuracarb, bendiocarb, furathiocarb, isoprocarb, metolcarb, xylylcarb, XMC and fenothiocarb;

nereistoxin derivatives such as cartap, thiocyclam, bensultap and thiosultap-sodium;

organic chlorine compounds such as dicofol, tetradifon, endosulfan, dienochlor and dieldrin;

organic metal compounds such as cyhexatin;

pyrethroid compounds such as fenvalerate, permethrin, cypermethrin, deltamethrin, cyhalothrin, tefluthrin, ethofenprox, flufenprox, cyfluthrin, fenpropathrin, flucythrinate, fluvalinate, cycloprothrin, lambda-cyhalothrin, pyrethrins, esfenvalerate, tetramethrin, resmethrin, protrifenbute, bifenthrin, zeta-cypermethrin, acrinathrin, alpha-cypermethrin, allethrin, gamma-cyhalothrin, theta-cypermethrin, tau-fluvalinate, tralomethrin, profluthrin, beta-cypermethrin, beta-cyfluthrin, metofluthrin, phenothrin, imidate and flumethrin;

benzoylurea compounds such as diflubenzuron, chlorfluazuron, teflubenzuron, flufenoxuron, triflumuron, hexaflumuron, lufenuron, novaluron, noviflumuron, bistrifluoron and fluazuron;

juvenile hormone-like compounds such as methoprene, pyriproxyfen, fenoxycarb and diofenolan; pyridazinone compounds such as pyridaben;

pyrazole compounds such as fenpyroximate, fipronil, tebufenpyrad, ethiprole, tolfenpyrad, acetoprole, pyrafluprole and pyriprole;

neonicotinoids such as imidacloprid, nitenpyram, acetamiprid, thiacloprid, thiamethoxam, clothianidin, nidinotefuran and dinotefuran;

hydrazine compounds such as tebufenozide, methoxyfenozide, chromafenozide and halofenozide;

pyridine compounds such as pyridaryl and flonicamid;

tetronic acid compounds such as spirodiclofen;

strobilurin compounds such as fluacrypyrim;

pyridinamine compounds such as flufenerim; dinitro compounds; organic sulfur compounds; urea compounds; triazine compounds; hydrazone compounds;

and besides, compounds such as buprofezin, hexythiazox, amitraz, chlordimeform, silafluofen, triazamate, pymetrozine, pyrimidifen, chlorfenapyr, indoxacarb, acequinocyl, etoxazole, cyromazine, 1,3-dichloropropene, diafenthiuron, benclothiaz, bifenazate, spiromesifen, spirotetramat, propargite, clofentezine, metaflumizone, flubendiamide, cyflumetofen, chlorantraniliprole, cyenopyrafen, pyrifluquinazone, fenazaquin, pyridaben, amidoflumet, chlorobenzoate, sulfluramid, hydramethylnon, metaldehyde, HGW-86, ryanodine, flufenerim, pyridalyl, spirodiclofen, verbutin, thiazolylcinnanonitrile and amidoflumet; AKD-1022 and IKA-2000.

Incidentally, the above-described compounds are those indicated by common names (including names during petition in a part thereof) or test codes.

In addition, microbe-origin pesticides such as insecticidal parasporal inclusions produced by *Bacillus thuringienses aizawai, Bacillus thuringienses kurstaki, Bacillus thuringienses israelensis, Bacillus thuringienses iaponensis, Bacillus thuringienses tenebrionis* or *Bacillus thuringienses*, entomopathogenic viruses, entomopathogenic fungi, and nematophagous fungi; antibiotics and semisynthetic antibiotics such as avermectin, emamectin benzoate, milbemectin, milbemycin, spinosad, ivermectin, lepimectin, DE-175, abamectin, emamectin and spinetoram; natural products such as azadirachtin and rotenone; and repellents such as deet may also be used by being mixed or combined with the optional active ingredients.

Incidentally, the above-described compounds are those indicated by common names (including names during petition in a part thereof) or test codes.

Examples of compounds making up active ingredients of the fungicides include anilinopyrimidine compounds such as mepanipyrim, pyrimethanil, cyprodinil and ferimzone; triazoropyrimidine compounds such as 5-chloro-6-(2,4,6-trifluorophenyl)-7-(4-methylpiperidin-1-yl) [1,2,4]-triazoro[1,5-a]pyrimidine;

pyridinamine compounds such as fluazinam;

azole compounds such as triadimefon, bitertanol, triflumizole, etaconazole, propiconazole, penconazole, flusilazole, myclobutanil, cyproconazole, tebuconazole, hexaconazole, furconazole-cis, prochloraz, metconazole, epoxiconazole, tetraconazole, oxpoconazole fumarate, sipconazole, prothioconazole, triadimenol, flutriafol, difenoconazole, fluquinconazole, fenbuconazole, bromuconazole, diniconazole, tricyclazole, probenazole, simeconazole, pefurazoate, ipconazole and imibenconazole;

quinoxaline compounds such as quinomethionate;

dithiocarbamate compounds such as maneb, zineb, mancozeb, polycarbamate, metiram, propineb and thiram;

organic chlorine compounds such as fthalide, chlorothalonil and quintozene;

imidazole compounds such as benomyl, thiophanate-methyl, carbendazim, thiabendazole, fuberiazole and cyazofamid;

cyanoacetamide compounds such as cymoxanil;

phenylamide compounds such as metalaxyl, metalaxyl-M, mefenoxam, oxadixyl, ofurace, benalaxyl, benalaxyl-M (alias kiralaxyl or chiralaxyl), furalaxyl and cyprofuram;

sulfenic acid compounds such as dichlofluanid;

copper compounds such as cupric hydroxide and oxine copper;

isoxazole compounds such as hymexazol;

organophosphorus compounds such as fosetyl-Al, tolclofos-methyl, S-benzyl-O,O-diisopropyl phosphorothioate, O-ethyl-S,S-diphenyl phosphoro-dithioate, aluminum-ethyl hydrogenphosphonate, edifenphos and iprobenfos;

N-halogenothioalkyl compounds such as captan, captafol and folpet;

dicarboximide compounds such as procymidone, iprodione and vinclozolin;

benzanilide compounds such as flutolanil, mepronil, zoxamide and tiadinil;

anilide compounds such as carboxin, oxycarboxin, thifluzamide, penthiopyrad, boscalid, bixafen, fluopyram, isotianil, and a mixture of 3-(difluoromethyl)-1-methyl-N-[(1RS,4SR,9RS)-1,2,3,4-tetrahydro-9-isopropyl-1,4-methanonaphthalen-5-yl]pyrazole-4-carboxamide and 3-(difluoromethyl)-1-methyl-N-[(1RS,4SR,9SR)-1,2,3,4-tetrahydro-9-isopropyl-1,4-methanonaphthalen-5-yl] pyrazole-4-carboxamide (isopyrazam);

piperazine compounds such as triforine;

pyridine compounds such as pyrifenox;

carbinol compounds such as fenarimol and flutriafol; piperidine compounds such as fenpropidin;

morpholine compounds such as fenpropimorph, spiroxamine and tridemorph;

organotin compounds such as fentin hydroxide and fentin acetate;

urea compounds such as pencycuron;

cinnamic acid compounds such as dimethomorph and flumorph;

phenyl carbamate compounds such as diethofencarb; cyanopyrrole compounds such as fludioxonil and fenpiclonil;

strobilurin compounds such as azoxystrobin, kresoxim-methyl, metominofen, trifloxystrobin, picoxystrobin, oryzastrobin, dimoxystrobin, pyraclostrobin and fluoxastrobin;

oxazolizinone compounds such as famoxadone;

thiazolecarboxamide compounds such as ethaboxam;

silylamide compounds such as silthiopham;

aminoacidamide carbamate compounds such as iprovalicarb, benthiavalicarb-isopropyl and methyl[S—(R,S)]-[3-(N-isopropoxycarbonylvalinyl)-amino]-3-(4-chloro-phenyl)-propanoate (valiphenal);

imidazolinone compounds such as fenamidone;

hydroxyanilide compounds such as fenhexamid;

benzenesulfonamide compounds such as flusulfamid;

oxime ether compounds such as cyflufenamid;

phenoxyamide compounds such as fenoxanil;

anthraquinone compounds;

crotonic compounds;

antibiotics such as validamycin, kasugamycin and polyoxins;

guanidine compounds such as iminoctadine and dodine;

4-quinolinol derivatives such as 2,3-dimethyl-6-t-butyl-8-fluoro-4-acetylquinoline; and cyanomethylene compounds such as 2-(2-fluoro-5-(trifluoro-methyl)phenylthio)-2-(3-(2-methoxyphenyl)thiazolidine-2-ylidene)acetonitrile.

Incidentally, the above-described compounds are those indicated by common names (including names during petition in a part thereof) or test codes of Japan Plant Protection Association.

In addition, other compounds such as pyribencarb, isoprothiolane, pyroquilon, diclomezine, quinoxyfen, propamocarb hydrochloride, chloropicrin, dazomet, metam-sodium,nicobifen,metrafenone,UBF-307,diclocymet, proquinazid, amisulbrom (alias amibromdole), mandipropamid, fluopicolide, carpropamid, meptyldinocap, 6-t-butyl-8-fluoro-2,3-dimethylquinolin-4-yl acetate may also be used by being mixed or combined with the optional active ingredients.

Incidentally, the above-described compounds are those indicated by common names (including names during petition in a part thereof) or test codes of Japan Plant Protection Association.

The content of such optional active ingredients is preferably 1:100 to 100:1 in terms of a mass ratio of (the total content of the propylene glycol fatty acid monoester and fenbutatin oxide) to (the content of the optional active ingredients).

The agrochemical composition for pest control according to the present invention may be used in various preparation forms such as an emulsifiable concentrate, dust, granules, wettable powder, water-dispersible granules, a suspension, a soluble concentrate, aerosol and paste.

The formulation of the agrochemical composition for pest control according to the present invention may be conducted by mixing the propylene glycol fatty acid monoester and fenbutatin oxide that are essential active ingredients, and optionally the adjuvants and/or the optional active ingredients and preparing the resultant mixture into a proper dosage form or also by diluting and mixing a preparation of a composition comprising the propylene glycol fatty acid monoester and a preparation of a composition comprising fenbutatin oxide as needed. Incidentally, general-purpose adjuvants may be used as the adjuvants.

The agrochemical composition for pest control according to the present invention, which has been prepared into the proper dosage form, may be used as it is. However, the preparation may also be diluted with a diluent such as water before use.

According to the agrochemical composition for pest control of the present invention of such constitution as described above, the propylene glycol fatty acid monoester and fenbutatin oxide are selectively combined as an essential active ingredient, so that a synergistic effect by the two compounds making up this essential active ingredient is produced to develop an excellent pest control action. As a result, a high control effect is achieved even when the composition is applied in a small amount. In addition, high activity is achieved against mites having low sensitivity to a miticide composed of the already existing mite control composition, and markedly excellent ovicidal activity is achieved against not only pest adults, pest pupae, pest larvae and mite nymphs, but also eggs of the mites.

Accordingly, according to the agrochemical composition for pest control of the present invention, an excellent control effect is achieved even on hyposensitive mites having reduced sensitivity to chemicals even when the composition is applied in a small amount, and an excellent ovicidal effect is achieved even on eggs of the mites.

In addition the agrochemical composition for pest control according to the present invention can be prepared by diluting and mixing the propylene glycol fatty acid monoester and fenbutatin oxide as needed, so that a preparation method thereof is easy.

Such an agrochemical composition for pest control according to the present invention has an excellent control action against agricultural pests.

Specifically, the composition is suitable for controlling mites, aphids, whiteflies and thrips among the agricultural pests, particularly excellent for control of mites and more suitable for controlling phytophagous mites among the mites.

Specific examples of the phytophagous mites include spider mites such as two-spotted spider mite (*Tetranychus urticae*), *Tetranychus cinnabarinus*, Kanzawa spider mite (*Tetranychus kanzawai*), citrus red mite (*Panonychus citri*), European red mite (*Panonychus ulmi*), clover mite (*Bryobia praetiosa*), brown mite (*Bryobia rubrioculus*), hawthorn spider mite (*Tetranychus viennensis*), *Eotetranychus sexmanaculatus*, Smith spider mite (*Eotetranychus smithi*), *Tuckerella pavoniformis*, apricot spider mite (*Eotetranychus boreus*), *Eotetranychus geniculatus*, chestnut spider mite (*Eotetranychus pruni*), walnut spider mite (*Eotetranychus uncatus*), cryptomeria spider mite (*Oligonychus hondoensis*), southern red mite (*Oligonychus ilicis*) and larch spider mite (*Oligonychus karamatus*);

false spider mites such as citrus flat mite (*Brevipalpus lewisi*), privet mite (*Brevipalpus obovatus*), pineapple false spider mite (*Dolichotetranychus florodanus*) and persimmon false spider mite (*Tenuipalpus zhizhilashviliae*); eriophyid mites such as pink citrus rust mite (*Aculops pelekassi*), grape rust mite (*Calepitrimerus vitis*), *Acaphylla theae*, dry bulb mite (*Aceria tulipae*), plum rust mite (*Aculus fockeui*), apple rust mite (*Aculus schlechtendali*), purple teamite (*Calacarus carinatus*), pear rust mite (*Epitrimerus pyri*) and japanese pear rust mite (*Eriophyes chibaensis*);

acaridae such as flour mite (*Acarus siro*), brown legged grain mite (*Aleuroglyphus ovatus*), bulbmite (*Rhizoglyphus robini*) and mold mite (*Tyrophagus putrescentiae*); and tarsonemid mites such as broad mite (*Polyphagotarsonemus latus*), cyclamen mite (*Phytonemus pallidus*) and *Tarsonemus bilobatus*.

Examples of the aphids include green peach aphid (*Myzus persicae* (Sulzer)) and cotton aphid (*Aphis gossypii* Glover).

Examples of the whiteflies include sweet potato whitefly (*Bemisia tabaci* (Gennadius)) and greenhouse whitefly (*Trialeurodes vaporariorum* Westwood).

Examples of the thrips include western flower thrips (*Frankliniella occidentalis* Pergande) and melon thrips (*Thrips palmi* Karny).

Examples of other agricultural insect pests than the mites, aphids, whiteflies and thrips include diamondback moth (*Plutella xylostella*), cabbage armyworm (*Mamestra brassicae*), common cutworm (*Spodoptera litura*), codlingmoth (*Cydia pomonella*), bollworm (*Heliothis zea*), tobacco budworm (*Heliothis virescens*), gypsy moth (*Lymantria dispar*), rice leafroller (*Cnaphalocrocis medinalis*), smaller tea tortrix (*Adoxophyes* sp.), Colorado potato beetle (*Leptinotarsa decemlineata*), cucurbit leaf beetle (*Aulacophora femoralis*), boll weevil (*Anthonomus grandis*), planthoppers, leafhoppers, scales, bugs, grasshoppers, anthomyiid flies, scarabs, black cutworm (*Agrotis ipsilon*), cutworm (*Agrotis segetum*) and ants.

In addition, examples of other agricultural pests include soil pests, such as plant parasitic nematodes such as root-knot nematodes (Meloidogynidae), cyst nematodes (Heteroderidae), root-lesion nematodes (Pratylenchidae), white-tip nematode (*Aphelenchoi desbesseyi*), strawberry bud nematode (*Nothotylenchus acris*) and pine wood nematode (*Bursaphelenchus xylophilus*); gastropods such as slugs and snails; and isopods such as pill bugs (*Armadillidium vulgare*) and pill bugs (*Porcellio scaber*).

Examples of other insect pests than the agricultural (insect) pests as the object of control by the agrochemical composition for pest control according to the present invention include hygienic insect pests such as tropical rat mite (*Ornithonyssus bacoti*), cockroaches, housefly (*Musca domestica*) and house mosquito (*Culex pipiens pallens*); stored grain insect such as angoumois grain moth (*Sitotroga cerealella*), adzuki bean weevil (*Callosobruchus chinensis*), red flour beetle (*Tribolium castaneum*) and mealworms; clothes insect pests such as casemaking clothes moth (*Tinea translucens*) and black carpet beetle (*Attagenus unicolor japonicus*); house and household insect pests such as subterranean termites; domestic mites such a mold mite (*Tyrophaqus putrescentiae*), *Dermatophagoides farinae* and *Chelacaropsis moorei*; and hygienic insect pests such as tropical rat mite (*Ornithonyssus bacoti*).

<Pest Control Method>

The pest control method according to the present invention comprises applying a propylene glycol fatty acid monoester and fenbutatin oxide to pests or a habitat of the pests in synergistically effective amounts, specifically, in proportions that a mass ratio of the propylene glycol fatty acid monoester to fenbutatin oxide is generally 1:150 to 150:1, preferably 1:100 to 100:1 though it may vary according to meteorological conditions, preparation forms, application seasons, application places, kinds and occurrence situations of pests, etc. and thus may not be indiscriminately defined.

In the pest control method according to the present invention, the mass ratio (the propylene glycol fatty acid monoester:fenbutatin oxide) in the case where the object of control is mites is generally 1:150 to 150:1, preferably 1:100 to 100:1 though it may vary according to meteorological conditions, preparation forms, application seasons, application places, kinds and occurrence situations of pests, etc. and thus may not be indiscriminately defined.

In the pest control method according to the present invention, a composition comprising the propylene glycol fatty acid monoester and fenbutatin oxide in specific proportions, i.e., the agrochemical composition for pest control according to the present invention is applied to the pests or the habitat of the pests. However, the propylene glycol fatty acid monoester and fenbutatin oxide may also be separately applied.

In the pest control method according to the present invention, the active ingredient concentrations of the propylene glycol fatty acid monoester and fenbutatin oxide that are essential active ingredients in the agrochemical composition for pest control applied are generally 1 to 5,000 ppm, preferably 1 to 2,000 ppm, more preferably 10 to 1,000 ppm and generally 1 to 5,000 ppm, preferably 1 to 2,000 ppm, more preferably 5 to 1,000 ppm, respectively, though the concentrations may vary according to meteorological conditions, preparation forms, application seasons, application places, kinds and occurrence situations of pests, etc. and thus may not be indiscriminately defined.

Incidentally, the respective active ingredient concentrations of the propylene glycol fatty acid monoester and fenbutatin oxide are not limited to the above respective ranges and may be suitably set according to application conditions (specifically, the dosage form of the composition used, an application method, an object of application, a time of application and an application place) and the inhabiting situation of pests.

The amount applied per unit area of the agrochemical composition for pest control is adjusted in such a manner that the amounts applied per unit area of the propylene glycol fatty acid monoester and fenbutatin oxide that are essential active ingredients become proper.

A specific application amount may vary according to meteorological conditions, preparation forms, application seasons, application places, kinds and occurrence situations of pests, etc. and thus may not be indiscriminately defined. However, the amount of the propylene glycol fatty acid monoester applied per hectare is generally 1 to 50,000 g, preferably 10 to 10,000 g. On the other hand, the amount of fenbutatin oxide applied per hectare is generally 1 to 50,000 g, preferably 5 to 10,000 g.

Incidentally, the amount of the agrochemical composition for pest control applied per unit area is not limited to the above range.

As a preferred embodiment of the pest control method according to the present invention, is mentioned a method of diluting and mixing a preparation (trade name: "Akaritacchi® EC", available from ISHIHARA SANGYO KAISHA, Ltd.) of a composition comprising 70% by mass of the propylene glycol fatty acid monoester and a preparation (trade name: "OSADAN FLOWABLE", product of BASF Agro Co., Ltd.) of a composition comprising 48.0% by mass of fenbutatin oxide in such a manner that a mass ratio of the propylene glycol fatty acid monoester to fenbutatin oxide falls within a desired range and applying the resultant mixture to pests or a habitat of the pests by a proper application method.

Examples of an object of application as the habitat of the pests include plants, soils and buildings.

However, the plants are representative of the object of application because the object of control by the agrochemical composition for pest control used is particularly phytophagous mites.

As a method for applying the agrochemical composition for pest control, may be used a conventionally known method.

Specific examples thereof include a method of applying the composition by spraying such as jetting, misting, atomizing or powder or grain scattering, and besides a method of directly applying the composition on the surface of the object of control or the object of application by coating, powdering, covering or the like. In addition, as a method for applying the composition to a soil in particular, is used a method by mixing, drenching or the like.

According to such a pest control method as described above, the agrochemical composition for pest control according to the present invention is used as a chemical for controlling pests, and this agrochemical composition for pest control has an excellent pest control effect, so that even when pests that are an object of control are hyposensitive mites having reduced sensitivity to chemicals, such mites can be efficiently controlled even with a small application amount. In addition, although the single use of the propylene glycol fatty acid monoester or fenbutatin oxide is difficult to control eggs of mites, a markedly excellent ovicidal effect is achieved by selectively combining these compounds for use.

Such a pest control method according to the present invention achieves an excellent control effect on pests of all stages of growth. Specifically, the object of control is at least one agricultural pests selected from the group consisting of mites, aphids, whiteflies and thrips, and the method is suitable for controlling these agricultural pests.

Furthermore, the method is more suitable for controlling mites, particularly phytophagous mites among these pests.

In other words, the pest control method according to the present invention is excellent in control of agricultural pests such as mite adults, mite larvae, mite nymphs and mite eggs; whitefly adults, whitefly larvae and whitefly eggs; thrips adults, thrips larvae and thrips pupae; and aphid adults and aphid larvae.

EXAMPLES

Specific Examples of the present invention will hereinafter be described. However, the present invention is not limited thereto.

The following Example 1 and Comparative Example 1 to Comparative Example 3 are examples where female adults of two-spotted spider mite were used as an object of control.

Tests in these Example 1 and Comparative Example 1 to Comparative Example 3 were performed at the same time. Each test was performed by 3 times, and results were indicated by average values thereof.

Example 1

"Akaritacchi® EC" (trade name, available from ISHIHARA SANGYO KAISHA, Ltd.) comprising a propylene glycol fatty acid monoester as an active ingredient and "OSADAN FLOWABLE" (trade name, product of BASF Agro Co., Ltd.) comprising fenbutatin oxide as an active ingredient were diluted with water and mixed to prepare a composition (hereinafter also referred to as "agrochemical composition (1) for pest control") in which the active ingredient concentration of the propylene glycol fatty acid monoester was 175 ppm, the active ingredient concentration of fenbutatin oxide was 120 ppm, and a mass ratio (propylene glycol fatty acid monoester:fenbutatin oxide) thereof was 1.458:1.

The content (total content of the propylene glycol fatty acid monoester and fenbutatin oxide) of an essential active ingredient in this agrochemical composition (1) for pest control is 0.0295 parts by mass, and the content of adjuvants is 99.9705 parts by mass.

A kidney bean leaf was sandwiched between a glass plate, on which filter paper had been placed, and a glass-made Munger-cell (inside diameter: 2×2 cm), and 50 female adults (those within 5 days age after emerging collected from a strawberry farm in Utsunomiya city) of two-spotted spider mite having reduced sensitivity to a miticide composed of an already existing mite control composition were released in the cell, thereby providing a stage (hereinafter also referred to as "test cell (1)") for control test.

After the agrochemical composition (1) for pest control in an amount corresponding to 200 liters per 10 a was sprayed in this test cell (1) by means of an insecticide sprayer and air-dried, the Munger-cell was covered with fine-mesh polyester gauze so as to close an opening of the cell. Thereafter, the cell was left for 7 days under conditions that 16 hours of a day were set to a light period, and the remaining 8 hours were set to a dark period in a thermostatic chamber set to conditions of a temperature of 25° C. and a humidity of 65%, and the surviving number of the female adults of two-spotted spider mite was then confirmed to calculate out a mortality based on the surviving number. The result is shown in Table 1.

Comparative Example 1

A mortality of female adults of two-spotted spider mite was calculated out in the same manner as in Example 1 except that a composition obtained by diluting "Akaritacchi® EC" (trade name, available from ISHIHARA SANGYO KAISHA, Ltd.) with water in such a manner that the active ingredient concentration of the propylene glycol fatty acid monoester is 175 ppm was used in place of the agrochemical composition (1) for pest control in Example 1. The result is shown in Table 1.

Comparative Example 2

A mortality of female adults of two-spotted spider mite was calculated out in the same manner as in Example 1 except that a composition obtained by diluting "OSADAN FLOWABLE" (trade name, product of BASF Agro Co., Ltd.) with water in such a manner that the active ingredient concentration of fenbutatin oxide is 120 ppm was used in place of the agrochemical composition (1) for pest control in Example 1. The result is shown in Table 1.

Comparative Example 3

A mortality of female adults of two-spotted spider mite was calculated out in the same manner as in Example 1 except that water in an amount corresponding to 200 liters per 10 a was sprayed in place of the agrochemical composition (1) for pest control in Example 1. The result is shown in Table 1.

TABLE 1

| | Active ingredient concentration (ppm) | | Mortality (%) | Corrected mortality (%) |
|---|---|---|---|---|
| | Propylene glycol fatty acid monoester | Fenbutatin oxide | | |
| Example 1 | 175 | 120 | 100 | 100 (99.0) |
| Comparative Example 1 | 175 | 0 | 93.8 | 92.6 |
| Comparative Example 2 | 0 | 120 | 88.6 | 86.4 |
| Comparative Example 3 | 0 | 0 | 16.1 | 0 |

In Table 1, a theoretical value of a corrected mortality of the female adults of two-spotted spider mite, which was obtained by using both propylene glycol fatty acid monoester and fenbutatin oxide and calculated out according to the Colby's formula based on a corrected mortality, which was obtained according to the Abbott's formula from the result of the mortality in each of Comparative Example 1 and Comparative Example 2 by correcting in such a manner that a mortality upon treatment (Comparative Example 3) with no chemical is 0, is shown in parentheses together with a corrected mortality (experimental value) in Example 1.

Incidentally, the theoretical value of the corrected mortality according to the Colby's formula was calculated out according to the following numerical expression (1).

[Expression 1]

$$\text{theoretical value} = (X_1 + Y_1) - (X_1 \times Y_1)/100 \quad \text{Numerical expression (1)}$$

[In the expression, $X_1$ is a corrected mortality (experimental value) related to the propylene glycol fatty acid monoester, and $Y_1$ is a corrected mortality (experimental value) related to fenbutatin oxide.]

The Abbott's formula is as shown by the following numerical expression (2).

Numerical expression (2)

$$\text{corrected mortality (\%)} = \frac{\left(\begin{array}{c}\text{"survival rate upon treatment with} \\ \text{no chemical " -- " survival rate} \\ \text{upon treatment with chemical"}\end{array}\right)}{\text{survival rate upon treatment with no chemical}} \times 100 \quad \text{[Expression 2]}$$

It is apparent from the results shown in Table 1 that the agrochemical composition (1) for pest control of Example 1 according to the present invention has an excellent control effect on the adults of two-spotted spider mite having reduced sensitivity to chemicals, and it is also apparent from comparison between the theoretical value and the experimental value that both propylene glycol fatty acid monoester and fenbutatin oxide are used in combination in the agrochemical composition (1) for pest control, whereby a synergistic effect is developed.

The following Example 2 and Comparative Example 4 to Comparative Example 6 are examples where larvae of two-spotted spider mite were used as an object of control.

Tests in these Example 2 and Comparative Example 4 to Comparative Example 6 were performed at the same time. Each test was performed by 3 times, and results were indicated by average values thereof.

Example 2

"Akaritacchi® EC" (trade name, available from ISHIHARA SANGYO KAISHA, Ltd.) comprising a propylene glycol fatty acid monoester as an active ingredient and "OSADAN FLOWABLE" (trade name, product of BASF Agro Co., Ltd.) comprising fenbutatin oxide as an active ingredient were diluted with water and mixed to prepare a composition (hereinafter also referred to as "agrochemical composition (2) for pest control") in which the active ingredient concentration of the propylene glycol fatty acid monoester was 140 ppm, the active ingredient concentration of fenbutatin oxide was 96 ppm, and a mass ratio (propylene glycol fatty acid monoester:fenbutatin oxide) thereof was 1.458:1.

The content (total content of the propylene glycol fatty acid monoester and fenbutatin oxide) of an essential active ingredient in this agrochemical composition (2) for pest control is 0.0236 parts by mass, and the content of adjuvants is 99.9764 parts by mass.

A kidney bean leaf was sandwiched between a glass plate, on which filter paper had been placed, and a glass-made Munger-cell (inside diameter: 2×2 cm), and 50 larvae (those collected from a strawberry farm in Utsunomiya city) of two-spotted spider mite having reduced sensitivity to an already existing miticide were released in the cell, thereby providing a stage (hereinafter also referred to as "test cell (2)") for control test.

After the agrochemical composition (2) for pest control in an amount corresponding to 200 liters per 10 a was sprayed in this test cell (2) by means of an insecticide sprayer and air-dried, the Munger-cell was covered with fine-mesh polyester gauze so as to close an opening of the cell. Thereafter, the cell was left for 7 days under conditions that 16 hours of a day were set to a light period, and the remaining 8 hours were set to a dark period in a thermostatic chamber set to conditions of a temperature of 25° C. and a humidity of 65%, and the surviving number of the larvae of two-spotted spider mite was then confirmed to calculate out a mortality based on the surviving number. The result is shown in Table 2.

Comparative Example 4

A mortality of larvae of two-spotted spider mite was calculated out in the same manner as in Example 2 except that a composition obtained by diluting "Akaritacchi® EC" (trade name, available from ISHIHARA SANGYO KAISHA, Ltd.) with water in such a manner that the active ingredient concentration of the propylene glycol fatty acid monoester is 140 ppm was used in place of the agrochemical composition (2) for pest control in Example 2. The result is shown in Table 2.

Comparative Example 5

A mortality of larvae of two-spotted spider mite was calculated out in the same manner as in Example 2 except that a composition obtained by diluting "OSADAN FLOWABLE" (trade name, product of BASF Agro Co., Ltd.) with water in such a manner that the active ingredient concentration of fenbutatin oxide is 96 ppm was used in place of the agrochemical composition (2) for pest control in Example 2. The result is shown in Table 2.

Comparative Example 6

A mortality of larvae of two-spotted spider mite was calculated out in the same manner as in Example 2 except that water in an amount corresponding to 200 liters per 10 a was sprayed in place of the agrochemical composition (2) for pest control in Example 2. The result is shown in Table 2.

TABLE 2

| | Active ingredient concentration (ppm) | | Mortality (%) | Corrected mortality (%) |
|---|---|---|---|---|
| | Propylene glycol fatty acid monoester | Fenbutatin oxide | | |
| Example 2 | 140 | 96 | 82.6 | 78.4 (55.4) |
| Comparative Example 4 | 140 | 0 | 54.5 | 43.5 |
| Comparative Example 5 | 0 | 96 | 36.3 | 21.1 |
| Comparative Example 6 | 0 | 0 | 19.4 | 0 |

In Table 2, a theoretical value of a corrected mortality of the larvae of two-spotted spider mite, which was obtained by using the two active ingredients (specifically, the propylene glycol fatty acid monoester and fenbutatin oxide) and calculated out according to the Colby's formula based on a corrected mortality, which was obtained according to the Abbott's formula from the result of the mortality in each of Comparative Example 4 and Comparative Example 5 by correcting in such a manner that a mortality upon treatment (Comparative Example 6) with no chemical is 0, is shown in parentheses together with a corrected mortality (experimental value) in Example 2.

It is apparent from the results shown in Table 2 that the agrochemical composition (2) for pest control of Example 2 according to the present invention has an excellent control effect on the larvae of two-spotted spider mite having reduced sensitivity to chemicals, and it is also apparent from comparison between the theoretical value and the experimental value that both propylene glycol fatty acid monoester and fenbutatin oxide are used in combination in the agrochemical composition (2) for pest control, whereby a synergistic effect is developed.

The following Example 3 and Comparative Example 7 to Comparative Example 9 are examples where eggs of two-spotted spider mite were used as an object of control.

Tests in these Example 3 and Comparative Example 7 to Comparative Example 9 were performed at the same time. Each test was performed by 3 times, and results were indicated by average values thereof.

Example 3

"Akaritacchi® EC" (trade name, available from ISHIHARA SANGYO KAISHA, Ltd.) comprising a propylene glycol fatty acid monoester as an active ingredient and "OSADAN FLOWABLE" (trade name, product of BASF Agro Co., Ltd.) comprising fenbutatin oxide as an active ingredient were diluted with water and mixed to prepare a composition (hereinafter also referred to as "agrochemical composition (3) for pest control") in which the active ingredient concentration of the propylene glycol fatty acid monoester was 350 ppm, the active ingredient concentration of fenbutatin oxide was 240 ppm, and a mass ratio (propylene glycol fatty acid monoester:fenbutatin oxide) thereof was 1.458:1.

The content (total content of the propylene glycol fatty acid monoester and fenbutatin oxide) of an essential active ingredient in this agrochemical composition (3) for pest control is 0.0590 parts by mass, and the content of adjuvants is 99.9410 parts by mass.

A kidney bean leaf was sandwiched between a glass plate, on which filter paper had been placed, and a glass-made Munger-cell (inside diameter: 2×2 cm), and 50 eggs (those collected from a strawberry farm in Utsunomiya city) of two-spotted spider mite having reduced sensitivity to an already existing miticide were placed in the cell, thereby providing a stage (hereinafter also referred to as "test cell (3)") for control test.

After the agrochemical composition (3) for pest control in an amount corresponding to 200 liters per 10 a was sprayed in this test cell (3) by means of an insecticide sprayer and air-dried, the Munger-cell was covered with fine-mesh polyester gauze so as to close an opening of the cell. Thereafter, the cell was left for 22 days under conditions that 16 hours of a day were set to a light period, and the remaining 8 hours were set to a dark period in a thermostatic chamber set to conditions of a temperature of 25° C. and a humidity of 65%, and the respective surviving numbers of the eggs of two-spotted spider mite, larvae hatched from the eggs and adults emerged from the larvae were then confirmed to calculate out a mortality of the eggs based on the surviving numbers. The result is shown in Table 3.

Comparative Example 7

A mortality of eggs of two-spotted spider mite was calculated out in the same manner as in Example 3 except that a composition obtained by diluting "Akaritacchi® EC" (trade name, available from ISHIHARA SANGYO KAISHA, Ltd.) with water in such a manner that the active ingredient concentration of the propylene glycol fatty acid monoester is 350 ppm was used in place of the agrochemical composition (3) for pest control in Example 3. The result is shown in Table 3.

Comparative Example 8

A mortality of eggs of two-spotted spider mite was calculated out in the same manner as in Example 3 except that a composition obtained by diluting "OSADAN FLOWABLE" (trade name, product of BASF Agro Co., Ltd.) with water in such a manner that the active ingredient concentration of fenbutatin oxide is 240 ppm was used in place of the agrochemical composition (3) for pest control in Example 3. The result is shown in Table 3.

Comparative Example 9

A mortality of eggs of two-spotted spider mite was calculated out in the same manner as in Example 3 except that water in an amount corresponding to 200 liters per 10 a was sprayed in place of the agrochemical composition (3) for pest control in Example 3. The result is shown in Table 3.

TABLE 3

| | Active ingredient concentration (ppm) | | Mortality (%) | Corrected mortality (%) |
|---|---|---|---|---|
| | Propylene glycol fatty acid monoester | Fenbutatin oxide | | |
| Example 3 | 350 | 240 | 94.7 | 94.5 (10.9) |
| Comparative Example 7 | 350 | 0 | 5.1 | 2.4 |
| Comparative Example 8 | 0 | 240 | 11.3 | 8.7 |
| Comparative Example 9 | 0 | 0 | 2.8 | 0 |

In Table 3, a theoretical value of a corrected mortality of the eggs of two-spotted spider mite, which was obtained by using the two active ingredients (specifically, the propylene glycol fatty acid monoester and fenbutatin oxide) and calculated out according to the Colby's formula based on a corrected mortality, which was obtained according to the Abbott's formula from the result of the mortality in each of Comparative Example 7 and Comparative Example 8 by correcting in such a manner that a mortality upon treatment (Comparative Example 9) with no chemical is 0, is shown in parentheses together with a corrected mortality (experimental value) in Example 3.

It is apparent from the results shown in Table 3 that the agrochemical composition (3) for pest control of Example 3 according to the present invention has an excellent control effect on the eggs of two-spotted spider mite having reduced sensitivity to chemicals, and it is also apparent from comparison between the theoretical value and the experimental value that both propylene glycol fatty acid monoester and fenbutatin oxide are used in combination in the agrochemical composition (3) for pest control, whereby a synergistic effect is developed.

The following Examples 4 to 46 and Comparative Examples 10 to 24 are examples where female adults of two-spotted spider mite were used as an object of control.

Tests in these Examples 4 to 46 and Comparative Examples 10 to 24 were performed at the same time. Each test was performed by 2 times, and results were indicated by average values thereof.

Examples 4 to 46

"Akaritacchi® EC" (trade name, available from ISHIHARA SANGYO KAISHA, Ltd.) comprising a propylene glycol fatty acid monoester as an active ingredient and "OSADAN FLOWABLE" (trade name, product of BASF Agro Co., Ltd.) comprising fenbutatin oxide as an active ingredient were diluted with water and mixed to prepare compositions (hereinafter also referred to as "agrochemical composition (4) for pest control" to "agrochemical composition (46) for pest control") of their corresponding formulations shown in Table 4.

A kidney bean leaf was sandwiched between a glass plate, on which filter paper had been placed, and a glass-made Munger-cell (inside diameter: 2×2 cm), and 18 to 27 female adults (those within 5 days age after emerging collected from a strawberry farm in Utsunomiya city) of two-spotted spider mite having reduced sensitivity to an already existing miticide were released in the cell, thereby providing a stage (hereinafter also referred to as "test cell (4)") for control test.

After each of the agrochemical composition (4) for pest control to the agrochemical composition (46) for pest control in an amount corresponding to 100 liters per 10 a was sprayed in this test cell (4) by means of an insecticide sprayer and air-dried, the Munger-cell was covered with fine-mesh polyester gauze so as to close an opening of the cell. Thereafter, the cell was left for 7 days under conditions that 16 hours of a day were set to a light period, and the remaining 8 hours were set to a dark period in a thermostatic chamber set to conditions of a temperature of 25° C. and a humidity of 65%, and the surviving number of the female adults of two-spotted spider mite was then confirmed to calculate out a mortality based on the surviving number. The results are shown in Table 4.

Comparative Examples 10 to 16

A mortality of female adults of two-spotted spider mite was calculated out in the same manner as in Example 4 except that each of compositions obtained by diluting "Akaritacchi® EC" (trade name, available from ISHIHARA SANGYO KAISHA, Ltd.) with water and having their corresponding active ingredient concentrations of the propylene glycol fatty acid monoester shown in Table 4 was used in place of the agrochemical composition (4) for pest control in Example 4. The results are shown in Table 4.

Comparative Examples 17 to 23

A mortality of female adults of two-spotted spider mite was calculated out in the same manner as in Example 4 except that each of compositions obtained by diluting "OSADAN FLOWABLE" (trade name, product of BASF Agro Co., Ltd.) with water and having their corresponding active ingredient concentrations of fenbutatin oxide shown in Table 4 was used in place of the agrochemical composition (4) for pest control in Example 4. The results are shown in Table 4.

Comparative Example 24

A mortality of female adults of two-spotted spider mite was calculated out in the same manner as in Example 4 except that water in an amount corresponding to 100 liters per 10 a was sprayed in place of the agrochemical composition (4) for pest control in Example 4. The result is shown in Table 4.

TABLE 4

|  |  | Active ingredient concentration of Propylene glycol fatty acid monoester | | | |
|---|---|---|---|---|---|
|  |  | 700 ppm | 350 ppm | 175 ppm | 87.5 ppm |
| Active ingredient concentration of Fenbutatin oxide | 700 ppm | Example 4<br>100%  100%<br>(98.2%) | Example 11<br>100%  100%<br>(97.7%) | Example 18<br>100%  100%<br>(92.9%) | Example 25<br>100%  100%<br>(85.2%) |
|  | 350 ppm | Example 5<br>100%  100%<br>(97.1%) | Example 12<br>100%  100%<br>(96.2%) | Example 19<br>100%  100%<br>(88.5%) | Example 26<br>100%  100%<br>(76.1%) |
|  | 175 ppm | Example 6<br>100%  100%<br>(96.3%) | Example 13<br>100%  100%<br>(95.3%) | Example 20<br>100%  100%<br>(85.7%) | Example 27<br>95.5%  95.4%<br>(70.3%) |
|  | 87.5 ppm | Example 7<br>100%  100%<br>(95.4%) | Example 14<br>100%  100%<br>(94.1%) | Example 21<br>93.2%  93.1%<br>(81.9%) | Example 28<br>89.4%  89.2%<br>(62.6%) |
|  | 43.8 ppm | Example 8<br>100%  100%<br>(94.5%) | Example 15<br>100%  100%<br>(93.0%) | Example 22<br>100%  100%<br>(78.5%) | Example 29<br>84.7%  84.4%<br>(55.4%) |
|  | 21.9 ppm | Example 9<br>100%  100%<br>(94.7%) | Example 16<br>100%  100%<br>(93.2%) | Example 23<br>91.0%  90.9%<br>(79.0%) | Example 30<br>78.5%  78.2%<br>(56.6%) |
|  | 5.47 ppm | Example 10<br>93.6%  93.5%<br>(92.1%) | Example 17<br>97.6%  97.6%<br>(90.0%) | Example 24<br>89.2%  89.0%<br>(69.2%) | Example 31<br>49.5%  48.6%<br>(36.2%) |
|  | 0 ppm | Comparative Example 10<br>91.5%  91.4% | Comparative Example 11<br>89.2%  89.0% | Comparative Example 12<br>66.7%  66.1% | Comparative Example 13<br>31.0%  29.8% |

|  |  | Active ingredient concentration of Propylene glycol fatty acid monoester | | | |
|---|---|---|---|---|---|
|  |  | 43.8 ppm | 21.9 ppm | 10.9 ppm | 0 ppm |
| Active ingredient concentration of Fenbutatin oxide | 700 ppm | Example 32<br>95.0%  94.9%<br>(82.3%) | Example 37<br>83.0%  82.7%<br>(81.2%) | Example 42<br>86.7%  86.5%<br>(81.1%) | Comparative Example 17<br>79.3%  79.0% |
|  | 350 ppm | Example 33<br>86.6%  86.4%<br>(71.3%) | Example 38<br>83.0%  82.7%<br>(69.6%) | Example 43<br>88.2%  88.0%<br>(69.4%) | Comparative Example 18<br>66.5%  66.0% |
|  | 175 ppm | Example 34<br>81.8%  81.5%<br>(64.3%) | Example 39<br>78.7%  78.3%<br>(62.2%) | Example 44<br>71.0%  70.5%<br>(61.9%) | Comparative Example 19<br>58.4%  57.7% |
|  | 87.5 ppm | Example 35<br>76.2%  75.8%<br>(55.0%) | Example 40<br>66.4%  65.8%<br>(52.3%) | Example 45<br>65.0%  64.4%<br>(52.0%) | Comparative Example 20<br>47.5%  46.6% |
|  | 43.8 ppm | Example 36<br>68.4%  67.8%<br>(46.4%) | Example 41<br>57.4%  56.7%<br>(43.2%) | Example 46<br>45.7%  44.8%<br>(42.9%) | Comparative Example 21<br>37.5%  36.5% |

TABLE 4-continued

| | | | | |
|---|---|---|---|---|
| 21.9 ppm | — | — | — | Comparative Example 22<br>39.2% 38.2% |
| 5.47 ppm | — | — | — | Comparative Example 23<br>10.6% 9.1% |
| 0 ppm | Comparative Example 14<br>17.0% 15.7% | Comparative Example 15<br>12.1% 10.6% | Comparative Example 16<br>11.5% 10.1% | Comparative Example 24<br>1.6% 0% |

In Table 4, in each column of Example 4 to Example 46 and Comparative Example 10 to Comparative Example 24, the result of the mortality is shown on a left side of the column, and a corrected mortality corrected according to the Abbott's formula in such a manner that a mortality upon treatment (Comparative Example 24) with no chemical is 0 is shown on a right side of the column as shown in the result of the mortality in each of Comparative Example 10 to Comparative Example 23. In addition, in each column of Example 4 to Example 46, a theoretical value of the corrected mortality of female adults of two-spotted spider mite, which was obtained by using the two active ingredients (specifically, the propylene glycol fatty acid monoester and fenbutatin oxide) and calculated out according to the Colby's formula based on the corrected mortality, is shown in parentheses together with the resultant corrected mortality (experimental value) on the right side of the column.

It is apparent from the results shown in Table 4 and comparison between the theoretical values and the experimental values that the agrochemical compositions for pest control of Examples 4 to 46 develop a synergistic effect at a wide variety of mass ratios by using both propylene glycol fatty acid monoester and fenbutatin oxide in combination and have an excellent control effect on the female adults of two-spotted spider mite having reduced sensitivity to chemicals.

The following Examples 47 to 49 and Comparative Examples 25 to 30 are examples where eggs of Kanzawa spider mite were used as an object of control.

Tests in these Examples 47 to 49 and Comparative Examples 25 to 30 were performed at the same time. Each test was performed by 3 times, and results were indicated by average values thereof.

Example 47

In this Example 47, an agrochemical composition (3) for pest control separately prepared according to the same process as in Example 3 was used as an agrochemical composition for pest control.

A kidney bean leaf was sandwiched between a glass plate, on which filter paper had been placed, and a glass-made Munger-cell (inside diameter: 2×2 cm), and 50 eggs of Kanzawa spider mite were placed in the cell, thereby providing a stage (hereinafter also referred to as "test cell (5)") for control test.

After the agrochemical composition (3) for pest control in an amount corresponding to 200 liters per 10 a was sprayed in this test cell (5) by means of an insecticide sprayer and air-dried, the Munger-cell was covered with fine-mesh polyester gauze so as to close an opening of the cell. Thereafter, the cell was left for 8 days under conditions that 16 hours of a day were set to a light period, and the remaining 8 hours were set to a dark period in a thermostatic chamber to conditions of a temperature of 25° C. and a humidity of 65%, and the respective surviving numbers of the eggs of Kanzawa spider mite, larvae hatched from the eggs and adults emerged from the larvae were then confirmed to calculate out a mortality of the eggs based on the surviving numbers. The result is shown in Table 5.

Example 48

"Akaritacchi® EC" (trade name, available from ISHIHARA SANGYO KAISHA, Ltd.) comprising a propylene glycol fatty acid monoester as an active ingredient and "OSADAN FLOWABLE" (trade name, product of BASF Agro Co., Ltd.) comprising fenbutatin oxide as an active ingredient were diluted with water and mixed to prepare a composition (hereinafter also referred to as "agrochemical composition (47) for pest control") in which the active ingredient concentration of the propylene glycol fatty acid monoester was 233 ppm, the active ingredient concentration of fenbutatin oxide was 160 ppm, and a mass ratio (propylene glycol fatty acid monoester:fenbutatin oxide) thereof was 1.456:1.

The content (total content of the propylene glycol fatty acid monoester and fenbutatin oxide) of an essential active ingredient in this agrochemical composition (47) for pest control is 0.0393 parts by mass, and the content of adjuvants is 99.9607 parts by mass.

A mortality of eggs of Kanzawa spider mite was calculated out in the same manner as in Example 47 except that the agrochemical composition (47) for pest control was used in place of the agrochemical composition (3) for pest control in Example 47. The result is shown in Table 5.

Example 49

"Akaritacchi® EC" (trade name, available from ISHIHARA SANGYO KAISHA, Ltd.) comprising a propylene glycol fatty acid monoester as an active ingredient and "OSADAN FLOWABLE" (trade name, product of BASF Agro Co., Ltd.) comprising fenbutatin oxide as an active ingredient were diluted with water and mixed to prepare a composition (hereinafter also referred to as "agrochemical composition (48) for pest control") in which the active ingredient concentration of the propylene glycol fatty acid monoester was 175 ppm, the active ingredient concentration of fenbutatin oxide was 160 ppm, and a mass ratio (propylene glycol fatty acid monoester:fenbutatin oxide) thereof was 1.094:1.

The content (total content of the propylene glycol fatty acid monoester and fenbutatin oxide) of an essential active ingredient in this agrochemical composition (48) for pest control is 0.0335 parts by mass, and the content of adjuvants is 99.9665 parts by mass.

A mortality of eggs of Kanzawa spider mite was calculated out in the same manner as in Example 47 except that the agrochemical composition (48) for pest control was used in place of the agrochemical composition (3) for pest control in Example 47. The result is shown in Table 5.

Comparative Examples 25 to 27

A mortality of eggs of Kanzawa spider mite was calculated out in the same manner as in Example 47 except that each of compositions obtained by diluting "Akaritacchi® EC" (trade name, available from ISHIHARA SANGYO KAISHA, Ltd.) with water and having their corresponding active ingredient concentrations of the propylene glycol fatty acid monoester shown in Table 5 was used in place of the agrochemical composition (3) for pest control in Example 47. The results are shown in Table 5.

Comparative Examples 28 and 29

A mortality of eggs of Kanzawa spider mite was calculated out in the same manner as in Example 47 except that each of compositions obtained by diluting "OSADAN FLOWABLE" (trade name, product of BASF Agro Co., Ltd.) with water and having their corresponding active ingredient concentrations of fenbutatin oxide shown in Table 5 was used in place of the agrochemical composition (3) for pest control in Example 47. The results are shown in Table 5.

Comparative Example 30

A mortality of eggs of Kanzawa spider mite was calculated out in the same manner as in Example 47 except that water in an amount corresponding to 100 liters per 10 a was sprayed in place of the agrochemical composition (3) for pest control in Example 47. The result is shown in Table 5.

TABLE 5

| | Active ingredient concentration (ppm) | | Mortality (%) |
|---|---|---|---|
| | Propylene glycol fatty acid monoester | Fenbutatin oxide | |
| Example 47 | 350 | 240 | 100 (81.8) |
| Example 48 | 233 | 160 | 100 (87.9) |
| Example 49 | 175 | 160 | 100 (87.6) |
| Comparative Example 25 | 350 | 0 | 9.2 |
| Comparative Example 26 | 233 | 0 | 2.0 |
| Comparative Example 27 | 175 | 0 | 0 |
| Comparative Example 28 | 0 | 240 | 80.0 |
| Comparative Example 29 | 0 | 160 | 87.6 |
| Comparative Example 30 | 0 | 0 | 0 |

In Table 5, a theoretical value of the mortality of eggs of Kanzawa spider mite, which was obtained by using the two active ingredients (specifically, the propylene glycol fatty acid monoester and fenbutatin oxide) and calculated out according to the Colby's formula based on the result of the mortality obtained in each of Comparative Example 25 to Comparative Example 30, is shown in parentheses together with the mortality (experimental value) in each of Example 47 to Example 49.

Incidentally, the theoretical value of the mortality according to the Colby's formula was calculated out according to the following numerical expression (3).

[Expression 3]

$$\text{theoretical value} = (X_2 + Y_2) - (X_2 \times Y_2)/100 \quad \text{Numerical expression (3)}$$

[In the expression, $X_2$ is a mortality (experimental value) related to the propylene glycol fatty acid monoester, and $Y_2$ is a mortality (experimental value) related to fenbutatin oxide.]

It is apparent from the results shown in Table 5 that the agrochemical compositions for pest control of Examples 47 to 49 have an excellent control effect on the eggs of Kanzawa spider mite, and it is also apparent from comparison between the theoretical value and the experimental value that both propylene glycol fatty acid monoester and fenbutatin oxide are used in combination in the agrochemical compositions for pest control of Examples 47 to 49, whereby a synergistic effect is developed.

The following Example 50 and Comparative Examples 31 to 33 are examples where the first instar nymphs of western flower thrips were used as an object of control.

Tests in these Example 50 and Comparative Examples 31 to 33 were performed at the same time. Each test was performed by 3 times, and results were indicated by average values thereof.

Example 50

In this Example 50, an agrochemical composition (3) for pest control separately prepared according to the same process as in Example 3 was used as an agrochemical composition for pest control.

A kidney bean leaf was sandwiched between a glass plate, on which filter paper had been placed, and a glass-made Munger-cell (inside diameter: 6×6 cm), and 15 first instar nymphs of western flower thrips were released in the cell, thereby providing a stage (hereinafter also referred to as "test cell (6)") for control test.

After the agrochemical composition (3) for pest control in an amount corresponding to 200 liters per 10 a was sprayed in this test cell (6) by means of an insecticide sprayer and air-dried, the Munger-cell was covered with fine-mesh polyester gauze so as to close an opening of the cell. Thereafter, the cell was left for 8 days under conditions that 16 hours of a day were set to a light period, and the remaining 8 hours were set to a dark period in a thermostatic chamber set to conditions of a temperature of 25° C. and a humidity of 65%, and the surviving number of the first instar nymphs of western flower thrips was then confirmed to calculate out a mortality based on the surviving number. The result is shown in Table 6.

Comparative Example 31

A mortality of the first instar nymphs of western flower thrips was calculated out in the same manner as in Example 50 except that a composition obtained by diluting "Akaritacchi® EC" (trade name, available from ISHIHARA SANGYO KAISHA, Ltd.) with water in such a manner that the active ingredient concentration of the propylene glycol fatty acid monoester is 350 ppm was used in place of the agrochemical composition (3) for pest control in Example 50. The result is shown in Table 6.

Comparative Example 32

A mortality of the first instar nymphs of western flower thrips was calculated out in the same manner as in Example 50 except that a composition obtained by diluting "OSADAN FLOWABLE" (trade name, product of BASF Agro Co., Ltd.) with water in such a manner that the active ingredient concentration of fenbutatin oxide is 240 ppm was used in place of the agrochemical composition (3) for pest control in Example 50. The result is shown in Table 6.

Comparative Example 33

A mortality of the first instar nymphs of western flower thrips was calculated out in the same manner as in Example 50 except that water in an amount corresponding to 200 liters per 10 a was sprayed in place of the agrochemical composition (3) for pest control in Example 1. The result is shown in Table 6.

TABLE 6

| | Active ingredient concentration (ppm) | | Mortality (%) | Corrected mortality (%) |
|---|---|---|---|---|
| | Propylene glycol fatty acid monoester | Fenbutatin oxide | | |
| Example 50 | 350 | 240 | 88.9 | 85.7 (62.1) |
| Comparative Example 31 | 350 | 0 | 35.6 | 17.1 |
| Comparative Example 32 | 0 | 240 | 64.4 | 54.3 |
| Comparative Example 33 | 0 | 0 | 22.2 | 0 |

In Table 6, a theoretical value of a corrected mortality of the first instar nymphs of western flower thrips, which was obtained by using the two active ingredients (specifically, the propylene glycol fatty acid monoester and fenbutatin oxide) and calculated out according to the Colby's formula based on a corrected mortality, which was obtained according to the Abbott's formula from the result of the mortality in each of Comparative Example 31 and Comparative Example 32 by correcting in such a manner that a mortality upon treatment (Comparative Example 33) with no chemical is 0, is shown in parentheses together with a corrected mortality (experimental value) in Example 50.

It is apparent from the results shown in Table 6 that the agrochemical composition (3) for pest control of Example 50 has an excellent control effect on the first instar nymphs of western flower thrips, and it is also apparent from comparison between the theoretical value and the experimental value that both propylene glycol fatty acid monoester and fenbutatin oxide are used in combination in the agrochemical composition (3) for pest control, whereby a synergistic effect is developed.

The following Example 51 and Comparative Examples 34 to 36 are examples where pupae of western flower thrips were used as an object of control.

Tests in these Example 51 and Comparative Examples 34 to 36 were performed at the same time. Each test was performed by 3 times, and results were indicated by average values thereof.

Example 51

In this Example 51, an agrochemical composition (3) for pest control separately prepared according to the same process as in Example 3 was used as an agrochemical composition for pest control.

A kidney bean leaf was sandwiched between a glass plate, on which filter paper had been placed, and a glass-made Munger-cell (inside diameter: 6×6 cm), and 11 to 17 pupae of western flower thrips were released in the cell, thereby providing a stage (hereinafter also referred to as "test cell (7)") for control test.

After the agrochemical composition (3) for pest control in an amount corresponding to 200 liters per 10 a was sprayed in this test cell (7) by means of an insecticide sprayer and air-dried, the Munger-cell was covered with fine-mesh polyester gauze so as to close an opening of the cell. Thereafter, the cell was left for 8 days under conditions that 16 hours of a day were set to a light period, and the remaining 8 hours were set to a dark period in a thermostatic chamber set to conditions of a temperature of 25° C. and a humidity of 65%, and the respective surviving numbers of the pupae of western flower thrips and emerged adults were then confirmed to calculate out a mortality based on the surviving numbers. The result is shown in Table 7.

Comparative Example 34

A mortality of pupae of western flower thrips was calculated out in the same manner as in Example 51 except that a composition obtained by diluting "Akaritacchi® EC" (trade name, available from ISHIHARA SANGYO KAISHA, Ltd.) with water in such a manner that the active ingredient concentration of the propylene glycol fatty acid monoester is 350 ppm was used in place of the agrochemical composition (3) for pest control in Example 51. The result is shown in Table 7.

Comparative Example 35

A mortality of pupae of western flower thrips was calculated out in the same manner as in Example 51 except that a composition obtained by diluting "OSADAN FLOWABLE" (trade name, product of BASF Agro Co., Ltd.) with water in such a manner that the active ingredient concentration of fenbutatin oxide is 240 ppm was used in place of the agrochemical composition (3) for pest control in Example 51. The result is shown in Table 7.

Comparative Example 36

A mortality of pupae of western flower thrips was calculated out in the same manner as in Example 51 except that water in an amount corresponding to 200 liters per 10 a was sprayed in place of the agrochemical composition (3) for pest control in Example 51. The result is shown in Table 7.

TABLE 7

| | Active ingredient concentration (ppm) | | Mortality (%) | Corrected mortality (%) |
|---|---|---|---|---|
| | Propylene glycol fatty acid monoester | Fenbutatin oxide | | |
| Example 51 | 350 | 240 | 97.8 | 97.6 (68.8) |
| Comparative Example 34 | 350 | 0 | 50.8 | 46.6 |
| Comparative Example 35 | 0 | 240 | 46.2 | 41.6 |
| Comparative Example 36 | 0 | 0 | 7.9 | 0 |

In Table 7, a theoretical value of a corrected mortality of the pupae of western flower thrips, which was obtained by using the two active ingredients (specifically, the propylene glycol fatty acid monoester and fenbutatin oxide) and calculated out according to the Colby's formula based on a corrected mortality, which was obtained according to the Abbott's formula from the result of the mortality in each of Comparative Example 34 and Comparative Example 35 by correcting in such a manner that a mortality upon treatment (Comparative Example 36) with no chemical is 0, is shown in parentheses together with a corrected mortality (experimental value) in Example 51.

It is apparent from the results shown in Table 7 that the agrochemical composition (3) for pest control of Example 51 has an excellent control effect on pupae of western flower thrips, and it is also apparent from comparison between the theoretical value and the experimental value that both propylene glycol fatty acid monoester and fenbutatin oxide are used in combination in the agrochemical composition (3) for pest control, whereby a synergistic effect is developed.

The following Examples 52 to 54 and Comparative Examples 37 to 42 are examples where the second instar nymphs of western flower thrips were used as an object of control.

Tests in these Examples 52 to 54 and Comparative Examples 37 to 42 were performed at the same time. Each test was performed by 3 times, and results were indicated by average values thereof.

Examples 52 to 54

In these Examples 52 to 54, an agrochemical composition (48) for pest control separately prepared according to the same process as in Example 49, an agrochemical composition (47) for pest control separately prepared according to the same process as in Example 48 and an agrochemical composition (3) for pest control separately prepared according to the same process as in Example 3 were respectively used as agrochemical compositions for pest control in Example 52, Example 53 and Example 54.

A kidney bean leaf was sandwiched between a glass plate, on which filter paper had been placed, and a glass-made Munger-cell (inside diameter: 6×6 cm), and 11 to 18 second instar nymphs of western flower thrips were released in the cell, thereby providing a stage (hereinafter also referred to as "test cell (8)") for control test.

After each of the agrochemical composition (3) for pest control, the agrochemical composition (47) for pest control and the agrochemical composition (48) for pest control in an amount corresponding to 200 liters per 10 a was sprayed in this test cell (8) by means of an insecticide sprayer and air-dried, the Munger-cell was covered with fine-mesh polyester gauze so as to close an opening of the cell. Thereafter, the cell was left for 7 days under conditions that 16 hours of a day were set to a light period, and the remaining 8 hours were set to a dark period in a thermostatic chamber set to conditions of a temperature of 25° C. and a humidity of 65%, and the surviving number of the second instar nymphs of western flower thrips was then confirmed to calculate out a mortality based on the surviving number. The results are shown in Table 8.

Comparative Examples 37 to 39

A mortality of the second instar nymphs of western flower thrips was calculated out in the same manner as in Example 52 except that each of compositions obtained by diluting "Akaritacchi® EC" (trade name, available from ISHIHARA SANGYO KAISHA, Ltd.) with water and having their corresponding active ingredient concentrations of the propylene glycol fatty acid monoester shown in Table 8 was used in place of the agrochemical composition (48) for pest control in Example 52. The results are shown in Table 8.

Comparative Examples 40 and 41

A mortality of the second instar nymphs of western flower thrips was calculated out in the same manner as in Example 52 except that each of compositions obtained by diluting "OSADAN FLOWABLE" (trade name, product of BASF Agro Co., Ltd.) with water and having their corresponding active ingredient concentrations of fenbutatin oxide shown in Table 8 was used in place of the agrochemical composition (48) for pest control in Example 52. The results are shown in Table 8.

Comparative Example 42

A mortality of the second instar nymphs of western flower thrips was calculated out in the same manner as in Example 52 except that water in an amount corresponding to 200 liters per 10 a was sprayed in place of the agrochemical composition (48) for pest control in Example 52. The result is shown in Table 8.

TABLE 8

| | Active ingredient concentration (ppm) | | Mortality (%) | Corrected mortality (%) |
| --- | --- | --- | --- | --- |
| | Propylene glycol fatty acid monoester | Fenbutatin oxide | | |
| Example 52 | 175 | 160 | 56.7 | 52.9 (34.7) |
| Example 53 | 233 | 160 | 59.7 | 56.1 (39.7) |
| Example 54 | 350 | 240 | 71.6 | 69.1 (39.0) |
| Comparative Example 37 | 175 | 0 | 8.8 | 0.8 |
| Comparative Example 38 | 233 | 0 | 15.8 | 8.4 |
| Comparative Example 39 | 350 | 0 | 15.6 | 8.2 |
| Comparative Example 40 | 0 | 160 | 39.5 | 34.2 |
| Comparative Example 41 | 0 | 240 | 38.9 | 33.5 |
| Comparative Example 42 | 0 | 0 | 8.1 | 0 |

In Table 8, a theoretical value of a corrected mortality of the second instar nymphs of western flower thrips, which was obtained by using the two active ingredients (specifically, the propylene glycol fatty acid monoester and fenbutatin oxide) and calculated out according to the Colby's formula based on a corrected mortality, which was obtained according to the Abbott's formula from the result of the mortality in each of Comparative Examples 37 to 41 by correcting in such a manner that a mortality upon treatment (Comparative Example 42) with no chemical is 0, is shown in parentheses together with a corrected mortality (experimental value) in each of Examples 52 to 54.

It is apparent from the results shown in Table 8 that the agrochemical compositions for pest control of Examples 52 to 54 have an excellent control effect on the second instar nymphs of western flower thrips, and it is also apparent from comparison between the theoretical value and the experimental value that both propylene glycol fatty acid monoester and fenbutatin oxide are used in combination in the agrochemical compositions for pest control of Examples 52 to 54, whereby a synergistic effect is developed.

The following Examples 55 to 57 and Comparative Examples 43 to 48 are examples where pupae of melon thrips were used as an object of control.

Tests in these Examples 55 to 57 and Comparative Examples 43 to 48 were performed at the same time. Each test was performed by 3 times, and results were indicated by average values thereof.

Examples 55 to 57

In these Examples 55 to 57, an agrochemical composition (48) for pest control separately prepared according to the same process as in Example 49, an agrochemical composition (47) for pest control separately prepared according to the same process as in Example 48 and an agrochemical composition (3) for pest control separately prepared according to the same process as in Example 3 were respectively used as agrochemical compositions for pest control in Example 55, Example 56 and Example 57.

A kidney bean leaf was sandwiched between a glass plate, on which filter paper had been placed, and a glass-made Munger-cell (inside diameter: 6×6 cm), and 11 to 17 pupae of melon thrips were released in the cell, thereby providing a stage (hereinafter also referred to as "test cell (9)") for control test.

After each of the agrochemical composition (3) for pest control, the agrochemical composition (47) for pest control and the agrochemical composition (48) for pest control in an amount corresponding to 200 liters per 10 a was sprayed in this test cell (9) by means of an insecticide sprayer and air-dried, the Munger-cell was covered with fine-mesh polyester gauze so as to close an opening of the cell. Thereafter, the cell was left for 7 days under conditions that 16 hours of a day were set to a light period, and the remaining 8 hours were set to a dark period in a thermostatic chamber set to conditions of a temperature of 25° C. and a humidity of 65%, and the respective surviving numbers of the pupae of melon thrips and emerged adults were then confirmed to calculate out a mortality based on the surviving numbers. The results are shown in Table 9.

Comparative Examples 43 to 45

A mortality of pupae of melon thrips was calculated out in the same manner as in Example 55 except that each of compositions obtained by diluting "Akaritacchi® EC" (trade name, available from ISHIHARA SANGYO KAISHA, Ltd.) with water and having their corresponding active ingredient concentrations of the propylene glycol fatty acid monoester shown in Table 9 was used in place of the agrochemical composition (48) for pest control in Example 55. The results are shown in Table 9.

Comparative Examples 46 and 47

A mortality of pupae of melon thrips was calculated out in the same manner as in Example 55 except that each of compositions obtained by diluting "OSADAN FLOWABLE" (trade name, product of BASF Agro Co., Ltd.) with water and having their corresponding active ingredient concentrations of fenbutatin oxide shown in Table 9 was used in place of the agrochemical composition (48) for pest control in Example 55. The results are shown in Table 8.

Comparative Example 48

A mortality of pupae of melon thrips was calculated out in the same manner as in Example 55 except that water in an amount corresponding to 200 liters per 10 a was sprayed in place of the agrochemical composition (48) for pest control in Example 55. The result is shown in Table 9.

TABLE 9

| | Active ingredient concentration (ppm) | | Mortality (%) | Corrected mortality (%) |
|---|---|---|---|---|
| | Propylene glycol fatty acid monoester | Fenbutatin oxide | | |
| Example 55 | 175 | 160 | 100 | 100 (64.8) |
| Example 56 | 233 | 160 | 100 | 100 (64.7) |
| Example 57 | 350 | 240 | 100 | 100 (73.5) |
| Comparative Example 43 | 175 | 0 | 4.6 | 1.9 |
| Comparative Example 44 | 233 | 0 | 4.4 | 1.6 |
| Comparative Example 45 | 350 | 0 | 7.8 | 5.1 |
| Comparative Example 46 | 0 | 160 | 65.1 | 64.1 |
| Comparative Example 47 | 0 | 240 | 72.9 | 72.1 |
| Comparative Example 48 | 0 | 0 | 2.8 | 0 |

In Table 9, a theoretical value of a corrected mortality of the pupae of melon thrips, which was obtained by using the two active ingredients (specifically, the propylene glycol fatty acid monoester and fenbutatin oxide) and calculated out according to the Colby's formula based on a corrected mortality, which was obtained according to the Abbott's formula from the result of the mortality in each of Comparative Examples 43 to 47 by correcting in such a manner that a mortality upon treatment (Comparative Example 48) with no chemical is 0, is shown in parentheses together with a corrected mortality (experimental value) in each of Examples 55 to 57.

It is apparent from the results shown in Table 9 that the agrochemical compositions for pest control of Examples 55 to 57 have an excellent control effect on pupae of melon thrips, and it is also apparent from comparison between the theoretical value and the experimental value that both propylene glycol fatty acid monoester and fenbutatin oxide are used in combination in the agrochemical compositions for pest control of Examples 55 to 57, whereby a synergistic effect is developed.

The following Examples 58 to 60 and Comparative Examples 49 to 54 are examples where adults (2 days age after emerging) of green peach aphid were used as an object of control.

Tests in these Examples 58 to 60 and Comparative Examples 49 to 54 were performed at the same time. Each test was performed by 3 times, and results were indicated by average values thereof.

Examples 58 to 60

In these Examples 58 to 60, an agrochemical composition (48) for pest control separately prepared according to the same process as in Example 49, an agrochemical composition (47) for pest control separately prepared according to the same process as in Example 48 and an agrochemical composition (3) for pest control separately prepared according to the same process as in Example 3 were respectively used as agrochemical compositions for pest control in Example 58, Example 59 and Example 60.

A radish leaf (cut into a size of 3 cm×3 cm) was placed in a test tube (diameter: 2 nm×20 cm), into which water had been poured, and 12 adults (2 days age after emerging) of green peach aphid were released on the radish leaf and left to stand for a day. After the number (existing number) of the adults of green peach aphid, which were feeding on the radish leaf, was confirmed on the next day, and each of the agrochemical composition (3) for pest control, the agrochemical composition (47) for pest control and the agrochemical composition (48) for pest control in an amount corresponding to 133 liters per 10 a was sprayed on both front and back surfaces of the radish leaf by means of a hand sprayer and air-dried, the test tube was left for 8 days under conditions that 16 hours of a day were set to a light period, and the remaining 8 hours were set to a dark period in a thermostatic chamber set to conditions of a temperature of 25° C. and a humidity of 47%, and the surviving number of the adults of green peach aphid was then confirmed to calculate out a mortality based on the surviving number. The results are shown in Table 10.

Comparative Examples 49 to 51

A mortality of adults of green peach aphid was calculated out in the same manner as in Example 58 except that each of compositions obtained by diluting "Akaritacchi® EC" (trade name, available from ISHIHARA SANGYO KAISHA, Ltd.) with water and having their corresponding active ingredient concentrations of the propylene glycol fatty acid monoester shown in Table 10 was used in place of the agrochemical composition (48) for pest control in Example 58. The results are shown in Table 10.

Comparative Examples 52 and 53

A mortality of adults of green peach aphid was calculated out in the same manner as in Example 58 except that each of compositions obtained by diluting "OSADAN FLOWABLE" (trade name, product of BASF Agro Co., Ltd.) with water and having their corresponding active ingredient concentrations of fenbutatin oxide shown in Table 10 was used in place of the agrochemical composition (48) for pest control in Example 58. The results are shown in Table 10.

Comparative Example 54

A mortality of adults of green peach aphid was calculated out in the same manner as in Example 58 except that water in an amount corresponding to 133 liters per 10 a was sprayed in place of the agrochemical composition (48) for pest control in Example 58. The result is shown in Table 10.

TABLE 10

| | Active ingredient concentration (ppm) | | Mortality (%) | Corrected mortality (%) |
| --- | --- | --- | --- | --- |
| | Propylene glycol fatty acid monoester | Fenbutatin oxide | | |
| Example 58 | 175 | 160 | 97.2 | 97.1 (60.1) |
| Example 59 | 233 | 160 | 88.9 | 88.6 (63.7) |
| Example 60 | 350 | 240 | 100 | 100 (47.0) |
| Comparative Example 49 | 175 | 0 | 30.6 | 28.6 |
| Comparative Example 50 | 233 | 0 | 52.8 | 51.5 |
| Comparative Example 51 | 350 | 0 | 41.7 | 40.0 |
| Comparative Example 52 | 0 | 160 | 27.8 | 25.7 |
| Comparative Example 53 | 0 | 240 | 36.1 | 34.3 |
| Comparative Example 54 | 0 | 0 | 2.8 | 0 |

In Table 10, a theoretical value of a corrected mortality of the adults of green peach aphid, which was obtained by using the two active ingredients (specifically, the propylene glycol fatty acid monoester and fenbutatin oxide) and calculated out according to the Colby's formula based on a corrected mortality, which was obtained according to the Abbott's formula from the result of the mortality in each of Comparative Examples 49 to 53 by correcting in such a manner that a mortality upon treatment (Comparative Example 54) with no chemical is 0, is shown in parentheses together with a corrected mortality (experimental value) in each of Examples 58 to 60.

It is apparent from the results shown in Table 10 that the agrochemical compositions for pest control of Examples 58 to 60 have an excellent control effect on adults of green peach aphid, and it is also apparent from comparison between the theoretical value and the experimental value that both propylene glycol fatty acid monoester and fenbutatin oxide are used in combination in the agrochemical compositions for pest control of Examples 58 to 60, whereby a synergistic effect is developed.

The following Example 61 and Comparative Examples 55 to 57 are examples where nymphs (one day age after birth) of green peach aphid were used as an object of control.

Tests in these Example 61 and Comparative Examples 55 to 57 were performed at the same time. Each test was performed by 4 times, and results were indicated by average values thereof.

Example 61

In this Example 61, an agrochemical composition (47) for pest control separately prepared according to the same process as in Example 48 was used as an agrochemical composition for pest control.

A radish leaf (cut into a size of 3 cm×3 cm) was placed in a test tube (diameter: 2 nm×20 cm), into which water had been poured, and 12 nymphs (one day age after birth) of green peach aphid were released on the radish leaf and left to stand for a day. After the number (surviving number) of the nymphs of green peach aphid, which were feeding on the radish leaf, was confirmed on the next day, and the agrochemical composition (47) for pest control in an amount corresponding to 133 liters per 10 a was sprayed on both front and back surfaces of the radish leaf by means of a hand sprayer and air-dried, the test tube was left for 8 days under conditions that 16 hours of a day were set to a light period, and the remaining 8 hours were set to a dark period in a thermostatic chamber set to conditions of a temperature of 25° C. and a humidity of 47%, and the surviving number of the nymphs of green peach aphid was then confirmed to calculate out a mortality based on the surviving number. The result is shown in Table 11.

Comparative Example 55

A mortality of nymphs of green peach aphid was calculated out in the same manner as in Example 61 except that a composition obtained by diluting "Akaritacchi® EC" (trade name, available from ISHIHARA SANGYO KAISHA, Ltd.) with water in such a manner that the active ingredient concentration of the propylene glycol fatty acid monoester is 233 ppm was used in place of the agrochemical composition (47) for pest control in Example 61. The result is shown in Table 11.

Comparative Example 56

A mortality of nymphs of green peach aphid was calculated out in the same manner as in Example 61 except that a composition obtained by diluting "OSADAN FLOWABLE" (trade name, product of BASF Agro Co., Ltd.) with water in such a manner that the active ingredient concentration of fenbutatin oxide is 160 ppm was used in place of the agrochemical composition (47) for pest control in Example 61. The result is shown in Table 11.

Comparative Example 57

A mortality of nymphs of green peach aphid was calculated out in the same manner as in Example 61 except that water in an amount corresponding to 133 liters per 10 a was sprayed in place of the agrochemical composition (47) for pest control in Example 61. The result is shown in Table 11.

TABLE 11

| | Active ingredient concentration (ppm) | | Mortality (%) | Corrected mortality (%) |
|---|---|---|---|---|
| | Propylene glycol fatty acid monoester | Fenbutatin oxide | | |
| Example 61 | 233 | 160 | 100 | 100 (35.1) |
| Comparative Example 55 | 233 | 0 | 6.7 | 3.4 |
| Comparative Example 56 | 0 | 160 | 35.0 | 32.8 |
| Comparative Example 57 | 0 | 0 | 3.3 | 0 |

In Table 11, a theoretical value of a corrected mortality of the nymphs of green peach aphid, which was obtained by using the two active ingredients (specifically, the propylene glycol fatty acid monoester and fenbutatin oxide) and calculated out according to the Colby's formula based on a corrected mortality, which was obtained according to the Abbott's formula from the result of the mortality in each of Comparative Examples 55 and 56 by correcting in such a manner that a mortality upon treatment (Comparative Example 57) with no chemical is 0, is shown in parentheses together with a corrected mortality (experimental value) in Example 61.

It is apparent from the results shown in Table 11 that the agrochemical composition (47) for pest control of Example 61 has an excellent control effect on nymphs of green peach aphid, and it is also apparent from comparison between the theoretical value and the experimental value that both propylene glycol fatty acid monoester and fenbutatin oxide are used in combination in the agrochemical composition (47) for pest control of Example 61, whereby a synergistic effect is developed.

The following Example 62 and Comparative Examples 58 to 60 are examples where the fourth instar larvae of sweet potato whitefly were used as an object of control.

Tests in these Example 62 and Comparative Examples 58 to 60 were performed at the same time. Each test was performed by 3 times, and results were indicated by average values thereof.

Example 62

In this Example 62, an agrochemical composition (3) for pest control separately prepared according to the same process as in Example 3 was used as an agrochemical composition for pest control.

After the agrochemical composition (3) for pest control in an amount corresponding to 200 liters per 10 a was sprayed on cucumber seedlings planted in a pot, which 95 to 142 fourth instar larvae of sweetpotato whitefly inhabited, by means of a hand sprayer and air-dried, the cucumber seedlings were left for 8 days under conditions that 16 hours of a day were set to a light period, and the remaining 8 hours were set to a dark period in a thermostatic chamber set to conditions of a temperature of 25° C. and a humidity of 65%, and the surviving number of the fourth instar larvae of sweetpotato whitefly was then confirmed to calculate out a mortality based on the surviving number. The result is shown in Table 12.

Comparative Example 58

A mortality of the fourth instar larvae of sweetpotato whitefly was calculated out in the same manner as in Example 62 except that a composition obtained by diluting "Akaritacchi® EC" (trade name, available from ISHIHARA SANGYO KAISHA, Ltd.) with water in such a manner that the active ingredient concentration of the propylene glycol fatty acid monoester is 350 ppm was used in place of the agrochemical composition (3) for pest control in Example 62. The result is shown in Table 12.

Comparative Example 59

A mortality of the fourth instar larvae of sweetpotato whitefly was calculated out in the same manner as in Example 62 except that a composition obtained by diluting "OSADAN FLOWABLE" (trade name, product of BASF Agro Co., Ltd.) with water in such a manner that the active ingredient concentration of fenbutatin oxide is 240 ppm was used in place of the agrochemical composition (3) for pest control in Example 62. The result is shown in Table 12.

Comparative Example 60

A mortality of the fourth instar larvae of sweetpotato whitefly was calculated out in the same manner as in Example 62 except that water in an amount corresponding to 200 liters per 10 a was sprayed in place of the agrochemical composition (3) for pest control in Example 62. The result is shown in Table 12.

TABLE 12

| | Active ingredient concentration (ppm) | | Mortality (%) | Corrected mortality (%) |
|---|---|---|---|---|
| | Propylene glycol fatty acid monoester | Fenbutatin oxide | | |
| Example 62 | 350 | 240 | 82.0 | 80.6 (50.3) |
| Comparative Example 58 | 350 | 0 | 22.0 | 16.0 |
| Comparative Example 59 | 0 | 240 | 45.0 | 40.8 |
| Comparative Example 60 | 0 | 0 | 7.1 | 0 |

In Table 12, a theoretical value of a corrected mortality of the fourth instar larvae of sweetpotato whitefly, which was obtained by using the two active ingredients (specifically, the propylene glycol fatty acid monoester and fenbutatin oxide) and calculated out according to the Colby's formula based on a corrected mortality, which was obtained according to the Abbott's formula from the result of the mortality in each of Comparative Examples 58 and 59 by correcting in such a manner that a mortality upon treatment (Comparative Example 60) with no chemical is 0, is shown in parentheses together with a corrected mortality (experimental value) in Example 62.

It is apparent from the results shown in Table 12 that the agrochemical composition (3) for pest control of Example 62 has an excellent control effect on the fourth instar larvae of sweetpotato whitefly, and it is also apparent from comparison between the theoretical value and the experimental value that both propylene glycol fatty acid monoester and fenbutatin oxide are used in combination in the agrochemical composition (3) for pest control of Example 62, whereby a synergistic effect is developed.

The following Example 63 and Comparative Examples 61 to 63 are examples where eggs of sweetpotato whitefly were used as an object of control.

Tests in these Example 63 and Comparative Examples 61 to 63 were performed at the same time. Each test was performed by 3 times, and results were indicated by average values thereof.

Example 63

In this Example 63, an agrochemical composition (3) for pest control separately prepared according to the same process as in Example 3 was used as an agrochemical composition for pest control.

After the agrochemical composition (3) for pest control in an amount corresponding to 200 liters per 10 a was sprayed on cucumber seedlings planted in a pot, on which 79 to 146 eggs of sweetpotato whitefly were attached, by means of a hand sprayer and air-dried, the cucumber seedlings were left for 19 days under conditions that 16 hours of a day were set to a light period, and the remaining 8 hours were set to a dark period in a thermostatic chamber set to conditions of a temperature of 25° C. and a humidity of 65%, and the respective surviving numbers of the eggs of sweetpotato whitefly, larvae hatched from the eggs and adults emerged from the larvae were then confirmed to calculate out a mortality of the eggs based on the surviving numbers. The result is shown in Table 13.

Comparative Example 61

A mortality of eggs of sweetpotato whitefly was calculated out in the same manner as in Example 63 except that a composition obtained by diluting "Akaritacchi® EC" (trade name, available from ISHIHARA SANGYO KAISHA, Ltd.) with water in such a manner that the active ingredient concentration of the propylene glycol fatty acid monoester is 350 ppm was used in place of the agrochemical composition (3) for pest control in Example 63. The result is shown in Table 13.

Comparative Example 62

A mortality of eggs of sweetpotato whitefly was calculated out in the same manner as in Example 63 except that a composition obtained by diluting "OSADAN FLOWABLE" (trade name, product of BASF Agro Co., Ltd.) with water in such a manner that the active ingredient concentration of fenbutatin oxide is 240 ppm was used in place of the agrochemical composition (3) for pest control in Example 63. The result is shown in Table 13.

Comparative Example 63

A mortality of eggs of sweetpotato whitefly was calculated out in the same manner as in Example 63 except that water in an amount corresponding to 200 liters per 10 a was sprayed in place of the agrochemical composition (3) for pest control in Example 63. The result is shown in Table 13.

TABLE 13

| | Active ingredient concentration (ppm) | | Mortality (%) | Corrected mortality (%) |
| --- | --- | --- | --- | --- |
| | Propylene glycol fatty acid monoester | Fenbutatin oxide | | |
| Example 63 | 350 | 240 | 74.1 | 72.2 (68.1) |
| Comparative Example 61 | 350 | 0 | 37.6 | 33.1 |
| Comparative Example 62 | 0 | 240 | 55.5 | 52.8 |
| Comparative Example 63 | 0 | 0 | 6.7 | 0 |

In Table 13, a theoretical value of a corrected mortality of the eggs of sweetpotato whitefly, which was obtained by using the two active ingredients (specifically, the propylene glycol fatty acid monoester and fenbutatin oxide) and calculated out according to the Colby's formula based on a corrected mortality, which was obtained according to the Abbott's formula from the result of the mortality in each of Comparative Examples 61 and 62 by correcting in such a manner that a mortality upon treatment (Comparative Example 63) with no chemical is 0, is shown in parentheses together with a corrected mortality (experimental value) in Example 63.

It is apparent from the results shown in Table 13 that the agrochemical composition (3) for pest control of Example 63 has an excellent control effect on eggs of sweetpotato whitefly, and it is also apparent from comparison between the theoretical value and the experimental value that both propylene glycol fatty acid monoester and fenbutatin oxide are used in combination in the agrochemical composition (3) for pest control of Example 63, whereby a synergistic effect is developed.

The following Examples 64 and 65 and Comparative Examples 64 to 68 are examples where the first instar nymphs of greenhouse whitefly were used as an object of control.

Tests in these Examples 64 and 65 and Comparative Examples 64 to 68 were performed at the same time. Each test was performed by 3 times, and results were indicated by average values thereof.

Examples 64 and 65

In these Examples 64 and 65, an agrochemical composition (47) for pest control separately prepared according to the same process as in Example 48 and an agrochemical composition (3) for pest control separately prepared according to the same process as in Example 3 were respectively used as agrochemical compositions for pest control in Example 64 and Example 65.

After each of the agrochemical composition (3) for pest control and the agrochemical composition (47) for pest control in an amount corresponding to 200 liters per 10 a was sprayed on kidney bean seedlings planted in a pot, which 72 to 129 first instar nymphs of greenhouse whitefly were feeding, by means of a hand sprayer and air-dried, the kidney bean seedlings were left for 17 days under conditions that 16 hours of a day were set to a light period, and the remaining 8 hours were set to a dark period in a thermostatic chamber set to conditions of a temperature of 25° C. and a humidity of 65%, and the surviving number of the first instar nymphs of greenhouse whitefly was then confirmed to calculate out a mortality based on the surviving numbers. The results are shown in Table 14.

Comparative Examples 64 and 65

A mortality of the first instar nymphs of greenhouse whitefly was calculated out in the same manner as in Example 64 except that each of compositions obtained by diluting "Akaritacchi® EC" (trade name, available from ISHIHARA SANGYO KAISHA, Ltd.) with water and having their corresponding active ingredient concentrations of the propylene glycol fatty acid monoester shown in Table 14 was used in place of the agrochemical composition (47) for pest control in Example 64. The results are shown in Table 14.

Comparative Examples 66 and 67

A mortality of the first instar nymphs of greenhouse whitefly was calculated out in the same manner as in Example 64 except that each of compositions obtained by diluting "OSADAN FLOWABLE" (trade name, product of BASF Agro Co., Ltd.) with water and having their corresponding active ingredient concentrations of fenbutatin oxide shown in Table 14 was used in place of the agrochemical composition (47) for pest control in Example 64. The results are shown in Table 14.

Comparative Example 68

A mortality of the first instar nymphs of greenhouse whitefly was calculated out in the same manner as in Example 64 except that water in an amount corresponding to 200 liters per 10 a was sprayed in place of the agrochemical composition (47) for pest control in Example 64. The result is shown in Table 14.

TABLE 14

| | Active ingredient concentration (ppm) | | Mortality (%) | Corrected mortality (%) |
|---|---|---|---|---|
| | Propylene glycol fatty acid monoester | Fenbutatin oxide | | |
| Example 64 | 233 | 160 | 92.8 | 92.5 (45.0) |
| Example 65 | 350 | 240 | 76.7 | 75.7 (48.6) |
| Comparative Example 64 | 233 | 0 | 18.7 | 15.2 |
| Comparative Example 65 | 350 | 0 | 23.3 | 20.0 |
| Comparative Example 66 | 0 | 160 | 37.8 | 35.1 |
| Comparative Example 67 | 0 | 240 | 38.3 | 35.7 |
| Comparative Example 68 | 0 | 0 | 4.1 | 0 |

In Table 14, a theoretical value of a corrected mortality of the first instar nymphs of greenhouse whitefly, which was obtained by using the two active ingredients (specifically, the propylene glycol fatty acid monoester and fenbutatin oxide) and calculated out according to the Colby's formula based on a corrected mortality, which was obtained according to the Abbott's formula from the result of the mortality in each of Comparative Examples 64 to 67 by correcting in such a manner that a mortality upon treatment (Comparative Example 68) with no chemical is 0, is shown in parentheses together with a corrected mortality (experimental value) in each of Examples 64 and 65.

It is apparent from the results shown in Table 14 that the agrochemical compositions for pest control of Examples 64 and 65 have an excellent control effect on the first instar nymphs of greenhouse whitefly, and it is also apparent from comparison between the theoretical value and the experimental value that both propylene glycol fatty acid monoester and fenbutatin oxide are used in combination in the agrochemical compositions for pest control of Examples 64 and 65, whereby a synergistic effect is developed.

The following Examples 66 and 67 and Comparative Examples 69 to 73 are examples where eggs of greenhouse whitefly were used as an object of control.

Tests in these Examples 66 and 67 and Comparative Examples 69 to 73 were performed at the same time. Each test was performed by 3 times, and results were indicated by average values thereof.

Examples 66 and 67

In these Examples 66 and 67, an agrochemical composition (47) for pest control separately prepared according to the same process as in Example 48 and an agrochemical composition (3) for pest control separately prepared according to the same process as in Example 3 were respectively used as agrochemical compositions for pest control in Example 66 and Example 67.

After each of the agrochemical composition (3) for pest control and the agrochemical composition (47) for pest control in an amount corresponding to 200 liters per 10 a was sprayed on kidney bean seedlings planted in a pot, on which 82 to 142 eggs of greenhouse whitefly were attached, by means of a hand sprayer and air-dried, the kidney bean seedlings were left for 20 days under conditions that 16 hours of a day were set to a light period, and the remaining 8 hours were set to a dark period in a thermostatic chamber set to conditions of a temperature of 25° C. and a humidity of 65%, and the respective surviving numbers of the eggs of greenhouse whitefly, larvae hatched from the eggs and adults emerged from the larvae were then confirmed to calculate out a mortality of the eggs based on the surviving numbers. The results are shown in Table 15.

Comparative Examples 69 and 70

A mortality of eggs of greenhouse whitefly was calculated out in the same manner as in Example 66 except that each of compositions obtained by diluting "Akaritacchi® EC" (trade name, available from ISHIHARA SANGYO KAISHA, Ltd.) with water and having their corresponding active ingredient concentrations of the propylene glycol fatty acid monoester shown in Table 15 was used in place of the agrochemical composition (47) for pest control in Example 66. The results are shown in Table 15.

Comparative Examples 71 and 72

A mortality of eggs of greenhouse whitefly was calculated out in the same manner as in Example 66 except that each of compositions obtained by diluting "OSADAN FLOWABLE" (trade name, product of BASF Agro Co., Ltd.) with water and having their corresponding active ingredient concentrations of fenbutatin oxide shown in Table 15 was used in place of the agrochemical composition (47) for pest control in Example 66. The results are shown in Table 15.

Comparative Example 70

A mortality of eggs of greenhouse whitefly was calculated out in the same manner as in Example 66 except that water in an amount corresponding to 200 liters per 10 a was sprayed in place of the agrochemical composition (47) for pest control in Example 66. The result is shown in Table 15.

TABLE 15

| | Active ingredient concentration (ppm) | | Mortality (%) | Corrected mortality (%) |
|---|---|---|---|---|
| | Propylene glycol fatty acid monoester | Fenbutatin oxide | | |
| Example 66 | 233 | 160 | 83.2 | 82.3 (31.2) |
| Example 67 | 350 | 240 | 86.7 | 86.0 (43.3) |
| Comparative Example 69 | 233 | 0 | 9.1 | 4.3 |
| Comparative Example 70 | 350 | 0 | 13.6 | 9.1 |
| Comparative Example 71 | 0 | 160 | 31.7 | 28.1 |
| Comparative Example 72 | 0 | 240 | 40.7 | 37.6 |
| Comparative Example 73 | 0 | 0 | 5.0 | 0 |

In Table 15, a theoretical value of a corrected mortality of the eggs of greenhouse whitefly, which was obtained by using the two active ingredients (specifically, the propylene glycol fatty acid monoester and fenbutatin oxide) and calculated out according to the Colby's formula based on a corrected mortality, which was obtained according to the Abbott's formula from the result of the mortality in each of Comparative Examples 69 to 72 by correcting in such a manner that a mortality upon treatment (Comparative Example 73) with no chemical is 0, is shown in parentheses together with a corrected mortality (experimental value) in each of Examples 66 and 67.

It is apparent from the results shown in Table 15 that the agrochemical compositions for pest control of Examples 66 and 67 have an excellent control effect on eggs of greenhouse whitefly, and it is also apparent from comparison between the theoretical value and the experimental value that both propylene glycol fatty acid monoester and fenbutatin oxide are used in combination in the agrochemical compositions for pest control of Examples 66 and 67, whereby a synergistic effect is developed.

The following Example 68 and Comparative Examples 74 to 76 are examples where pupae of western flower thrips were used as an object of control.

Tests in these Example 68 and Comparative Examples 74 to 76 were performed at the same time. Each test was performed by 3 times, and results were indicated by average values thereof.

Example 68

An aqueous solution containing 1% by mass of a mixed liquid (containing 99.9% by mass of acetone and 0.1% by mass of "Toriton X100") of acetone and a surfactant "Toriton X100" (product of Sigma Product) was used as a solvent to prepare a composition (hereinafter also referred to as "agrochemical composition (49) for pest control") in which the concentration of a propylene glycol fatty acid monoester was 350 ppm, the concentration of fenbutatin oxide was 240 ppm, and a mass ratio (propylene glycol fatty acid monoester: fenbutatin oxide) thereof was 1.458:1.

The content (total content of the propylene glycol fatty acid monoester and fenbutatin oxide) of an essential active ingredient in this agrochemical composition (49) for pest control is 0.0590 parts by mass, and the content of adjuvants is 99.9410 parts by mass.

A kidney bean leaf was sandwiched between a glass plate, on which filter paper had been placed, and a glass-made Munger-cell (inside diameter: 6×6 cm), and 12 to 25 pupae of western flower thrips were released in the cell, thereby providing a stage (hereinafter also referred to as "test cell (10)") for control test.

After the agrochemical composition (49) for pest control in an amount corresponding to 200 liters per 10 a was sprayed in this test cell (10) by means of an insecticide sprayer and air-dried, the Munger-cell was covered with fine-mesh polyester gauze so as to close an opening of the cell. Thereafter, the cell was left for 7 days under conditions that 16 hours of a day were set to a light period, and the remaining 8 hours were set to a dark period in a thermostatic chamber set to conditions of a temperature of 25° C. and a humidity of 65%, and the respective surviving numbers of the pupae of western flower thrips and emerged adults were then confirmed to calculate out a mortality of the pupae based on the surviving numbers. The result is shown in Table 16.

Comparative Example 74

A mortality of pupae of western flower thrips was calculated out in the same manner as in Example 68 except that a composition comprising the propylene glycol fatty acid monoester at an active ingredient concentration of 350 ppm was used in place of the agrochemical composition (49) for pest control in Example 68. The result is shown in Table 16.

Comparative Example 75

A mortality of pupae of western flower thrips was calculated out in the same manner as in Example 68 except that a composition comprising fenbutatin oxide at an active ingredient concentration of 240 ppm was used in place of the agrochemical composition (49) for pest control in Example 68. The result is shown in Table 16.

Comparative Example 76

A mortality of pupae of western flower thrips was calculated out in the same manner as in Example 68 except that a solution containing 1% of mixed liquid of aceton-toriton in an amount corresponding to 200 liters per 10 a was sprayed in place of the agrochemical composition (49) for pest control in Example 68. The result is shown in Table 16.

TABLE 16

| | Active ingredient concentration (ppm) | | Mortality (%) | Corrected mortality (%) |
|---|---|---|---|---|
| | Propylene glycol fatty acid monoester | Fenbutatin oxide | | |
| Example 68 | 350 | 240 | 85.5 | 84.1 (56.2) |
| Comparative Example 74 | 350 | 0 | 24.9 | 17.6 |
| Comparative Example 75 | 0 | 240 | 51.5 | 46.8 |
| Comparative Example 76 | 0 | 0 | 8.9 | 0 |

In Table 16, a theoretical value of a corrected mortality of the pupae of western flower thrips, which was obtained by using the two active ingredients (specifically, the propylene glycol fatty acid monoester and fenbutatin oxide) and calculated out according to the Colby's formula based on a corrected mortality, which was obtained according to the Abbott's formula from the result of the mortality in each of Comparative Example 74 and 75 by correcting in such a manner that a mortality upon treatment (Comparative Example 76) with no chemical is 0, is shown in parentheses together with a corrected mortality (experimental value) in Example 68.

It is apparent from the results shown in Table 16 that the agrochemical composition (49) for pest control of Example 68 has an excellent control effect on pupae of western flower thrips, and it is also apparent from comparison between the theoretical value and the experimental value that both propylene glycol fatty acid monoester and fenbutatin oxide are used in combination in the agrochemical composition (49) for pest control, whereby a synergistic effect is developed.

The invention claimed is:

1. An agrochemical composition for pest control comprising a propylene glycol fatty acid monoester and fenbutatin oxide.

2. The agrochemical composition for pest control according to claim 1, wherein a mass ratio of the propylene glycol fatty acid monoester to fenbutatin oxide is 1:150 to 150:1.

3. A pest control method comprising applying a propylene glycol fatty acid monoester and fenbutatin oxide to pests or a habitat of the pests.

4. The pest control method according to claim 3, wherein a mass ratio of the propylene glycol fatty acid monoester to fenbutatin oxide is 1:150 to 150:1.

5. The pest control method according to claim 3, wherein the habitat of the pests is a plant.

6. The pest control method according to claim 3, wherein the pests are agricultural pests.

7. The pest control method according to claim 6, wherein the pests comprise at least one agricultural pest selected from the group consisting of mites, aphids, whiteflies and thrips.

8. The pest control method according to claim 7, wherein the pests are mites.

9. The pest control method according to claim 8, wherein the pests are phytophagous mites.

10. The pest control method according to claim 8, wherein the pests are hyposensitive mites having reduced sensitivity to chemicals.

11. The pest control method according to claim 8, wherein the pests are eggs of the mites.

12. The pest control method according to claim 7, wherein the pests are whiteflies.

13. The pest control method according to claim 7, wherein the pests are thrips.

14. The pest control method according to claim 7, wherein the pests are aphids.

* * * * *